United States Patent
Willey et al.

(10) Patent No.: US 11,628,470 B2
(45) Date of Patent: Apr. 18, 2023

(54) METHOD FOR LOCATING ELEMENTS ON A FLEXIBLE ULTRASOUND PHASED ARRAY

(71) Applicant: Government of the United States as Represented by the Secretary of the Air Force, Wright-Patterson AFB, OH (US)

(72) Inventors: Carson L Willey, Beavercreek, OH (US); Abigail T Juhl, Washington Township, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 258 days.

(21) Appl. No.: 16/899,045

(22) Filed: Jun. 11, 2020

(65) Prior Publication Data

US 2020/0391244 A1 Dec. 17, 2020

Related U.S. Application Data

(60) Provisional application No. 62/861,450, filed on Jun. 14, 2019.

(51) Int. Cl.
*G01S 15/89* (2006.01)
*B06B 1/02* (2006.01)
(Continued)

(52) U.S. Cl.
CPC .......... *B06B 1/0215* (2013.01); *B06B 1/0607* (2013.01); *G01S 15/8936* (2013.01); *A61B 8/4461* (2013.01); *A61B 8/4494* (2013.01)

(58) Field of Classification Search
CPC .................................................... G01S 5/8936
See application file for complete search history.

(56) References Cited

U.S. PATENT DOCUMENTS

| 8,914,269 | B2 | 12/2014 | Dutta |
| 9,689,671 | B2 | 6/2017 | Instanes |

(Continued)

FOREIGN PATENT DOCUMENTS

| WO | 2014120917 | 8/2014 |
| WO | 2019046550 | 3/2019 |

OTHER PUBLICATIONS

T. Stratoudaki et al., "Full matrix capture and the total focusing imaging algorithm using laser induced ultrasonic phased arrays," AIP Conf. Proc., vol. 1806 (2017) 9 pages total.

(Continued)

*Primary Examiner* — Rochelle D Turchen
(74) *Attorney, Agent, or Firm* — AFMCLO/JAZ; Chastity D. S. Whitaker

(57) ABSTRACT

A method for locating a plurality of elements comprising a flexible ultrasound phased array. The method includes constructing a matrix of traveltimes by iteratively transmitting a signal from one element of the plurality and receiving the signal at each of the other elements of the plurality. Traveltimes are derived from each received signal and arrayed in a matrix. Relative positions of the first element of the plurality and the last element of the plurality are established and the locations of the remaining elements of the plurality are iteratively modeled to fit the matrix of traveltimes.

16 Claims, 22 Drawing Sheets
(14 of 22 Drawing Sheet(s) Filed in Color)

(51) Int. Cl.
*B06B 1/06* (2006.01)
*A61B 8/00* (2006.01)

(56) References Cited

U.S. PATENT DOCUMENTS

| | | |
|---|---|---|
| 10,576,499 B2 | 3/2020 | Liu |
| 2013/0283918 A1 | 10/2013 | Habermehl |
| 2016/0038119 A1* | 2/2016 | Desjardins ........... A61B 8/4444 |
| | | 600/424 |
| 2019/0128856 A1 | 5/2019 | Spay |
| 2021/0282748 A1* | 9/2021 | Stehle ................. G01S 15/8915 |

OTHER PUBLICATIONS

C. Willey et al., "A two-dimensional analysis of the sensitivity of a pulse first break to wave speed contrast on a scale below the resolution length of ray tomography," J. Acoust. Soc. Am., vol. 139 (2016) 3145-3158.

C. Holmes et al., "Post-processing of the full matrix of ultrasonic transmit-receive array data for non-destructive evaluation," NDT&E Int'l, vol. 38 (2005) 701-711.

R. Sleeman et al., "Robust automatic P-phase picking: an on-line implementation in the analysis of broadband seismogram recordings," Physics of the Earth and Planetary Interiors, vol. 113 (1999) 265-275.

C. Saragiotis et al., "Automatic traveltime-picking using the instantaneous traveltime," Geophysics, vol. 78 (2013) 53-58.

* cited by examiner

METHOD FOR LOCATING ELEMENTS ON A FLEXIBLE ULTRASOUND PHASED ARRAY

Pursuant to 37 C.F.R. § 1.78(a)(4), this application claims the benefit of and priority to prior filed Provisional Application Ser. No. 62/861,450, filed Jun. 14, 2019, which is expressly incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to image reconstruction and, more particularly, to ultrasound image reconstruction.

BACKGROUND OF THE INVENTION

Ultrasound, defined as high frequency sound waves (i.e., 20 kHz up to several GHz), may be used in detecting or observing objects, measuring distances, or imaging subsurface features. A commonly known use of ultrasound is in sonography, a medical imaging technique that uses ultrasound waves for in vivo imaging. However, ultrasound has found application in geophysical prospecting (seismological imaging), ocean floor studies (sonar imaging), and nondestructive testing and evaluation (phased array ultrasonic imaging).

FIG. 1 illustrates a conventional sonograph machine 50; FIG. 2A displays a hand-held, linear ultrasound transducer 52 conventionally used with in sonography; and FIG. 2B shows a flexible ultrasound transducer 54. The sonograph machine 50 utilizes the transducer array (whether it is the examples of FIG. 2A or 2B or other known transducer array configurations) to send and receive ultrasound waves. Parameters of the ultrasound waves may be manipulated from a control panel 56, which may be coupled to a display 58 for displaying a reconstructed image 60 generated by a computer 62 from ultrasound waves received by the transducer 52, 54. Oftentimes, particularly for obstetric sonography but not shown in FIG. 1, a printer may be included. The transducer shape and size varies upon the application and intended use. For example, in FIG. 2A, the hand held transducer 52 may be used for obstetric procedures as the sound waves diverge in transmission. The hand-held transducer 52 includes a housing 64 that surrounds a transducer array (oftentimes, a piezoelectric crystal but not shown in FIG. 2A), a linear acoustic window 66 through which ultrasound waves are transmitted to and from the transducer array, and a cable 68 configured to supply power to the transducer 52 and to transmit information between the transducer 52, the computer 62, and the control panel 56. However, it would be advantageous for the transducer to conform to the shape of the anatomy, or more generally the domain, to be imaged for remote or long-term monitoring; therefore, the flexible transducer 54, such as the one illustrated in FIG. 2B, may be desirable. The flexible transducer 54 includes a housing 70 (surrounding operational components) that is coupled to a flexible substrate 72 in which a transducer array is embedded (not shown), and a cable 74 configured to supply power to the transducer 54 and to transmit information between the transducer 54, the computer 62, and the control panel 56.

Whether ultrasound imaging is accomplished via hand-held or flexible transducers 52, 54 (such as those illustrated in FIG. 2A or 2B) or a series of separate transducers spaced away from one another but operably coupled, data acquisition methodology is similar. A wavefield is excited (transmitted) from at least one point in space (a transmitter) and sampled (received) at a plurality of points in space (receivers, transmitters, i.e., the array elements) that are spatially distributed across a boundary of the domain to be interrogated. By collecting signals from different combinations of transmitters and receivers, and subsequently post-processing the signals, a dataset (used as an input to an imaging algorithm) may be built. The dataset and imaging algorithm require an exact knowledge of the location of the array elements in space (i.e., parameters of the system). Any errors in the system parameters may cause distortion in the resulting reconstruction.

Ultrasound image formation from the conventional, flat, hand-held transducer 52 (FIG. 2A) is well understood and widely utilized. Such image formation methods may be classified as either quantitative or qualitative, depending on whether the method generates parameter maps of physical quantities or intensity-based representations corresponding to structural features (e.g., cracks, holes, or other internal features). FIG. 3 illustrates a one-dimensional linear array in a Cartesian defined coordinate system, {o, x, y}, that corresponds to the transducer 52 of FIG. 2A. A first element (star $r_{T1}$) of a linear array acting as a transmitter (as well as a receiver) and other elements of the linear array acting (hexagons $r_{R2}$, $r_{R3}$, $r_{R4}$, $r_{R5}$, $r_{R6}$) as receivers to image a point (P, which may be an anatomical feature) with a transmitted ray (solid line arrow) and scattered rays, or wavepaths (dashed line arrows), illustrated. The wavefields of all transmitters ($r_{T1}$) and receivers ($r_{R2}$, $r_{R3}$, $r_{R4}$, $r_{R5}$, $r_{R6}$) are focused at the point (P) of the image algorithmically rather than physically. An expression for traveltime of the wavefield from the transmitter location, $r_T$, to the point, $r_P$, and then back to a receiver point, $r_R$, may be written:

$$t(r_T, r_R, r_P) = \frac{|r_T - r_P| + |r_P - r_R|}{c}, \quad (1)$$

where $r = \{x\ y\}^t$ is a position vector, $|\bullet|$ is the magnitude operator, c is the background wave speed, and the subscripts, T, R, and P indicate the index of the transmitter, the receiver, and the point in the image, respectively. A conventional, total focusing method ("TFM") time domain beamforming algorithm, based on full matrix capture ("FMC") may then be written:

$$I(r_P) = \left| \sum_{R=1}^{N_R} \sum_{T=1}^{N_T} h_{RT}(t(r_T, r_R, r_P)) \right|, \quad (2)$$

where I is an image point intensity, $h_{RT}$ is the Hilbert transform of the signal resulting from transmitting at $r_T$ and receiving at $r_R$. The Hilbert transform of the signal is used rather than the signal, itself, because the Hilbert transform gives a complex valued signal leading to better destructive interference of signal portions when out of phase and better constructive interference of in phase signal portions. This TFM technique, described in C. HOLMES et al., "Post-processing of the full matrix of ultrasonic transmit-receive array data for non-destructive evaluation," NDT&E Int'l, Vol. 38 (2005), is used as a testbed code to demonstrate the effectiveness of a transducer location algorithm. Other conventional imaging algorithms, such as: frequency domain beamforming or diffraction tomography, super-resolution techniques, ray-based tomography, full wave inversion, etc. may also have been used.

Performing ultrasound imaging on non-flat surfaces can be challenging if using the conventional, rigid, flat transducer 52 of FIG. 2A. For an object 76 having a complex shape (or an embedded flaw 78), conventional methods for nondestructive evaluation have included embedding the object 76 in a container 80 filled with liquid water bath or other media 82 (i.e., immersion testing, as in FIG. 4). Once the object 76 is surrounded by a homogeneous background medium 82 bound by flat walls of the container 80, a linear transducer 84 may be used to transmit (solid arrows) and receive (dashed arrows) ultrasound waves. A similar implementation has been used to develop multiple breast cancer screening technologies. Another recent development is the use of ice (as opposed to liquid) as an encasing medium, which has been termed cryo-ultrasonics. Once the ice has formed, a rigid transducer array may be scanned around the flat surface of the ice. One advantage to using ice is that it has a better impedance match to the high strength objects commonly inspected in nondestructive testing.

Still another conventional technique, not shown here, is the so-called water-wedge. The water-wedge includes a bladder filled with water and attached to the front of a rigid transducer array. The bladder conforms to the surface of the object and may fill gaps between the object and the array face. While these phased array ultrasonic testing ("PAUT") systems do provide a somewhat conformal surface, the system size grows quite large, which restricts usability in some cases. Yet another conventional method for imaging an object having a complex geometry is to use a flexible array that may conform to the surface of the object (such as the transducer 54 of FIG. 2B) such that the array element positions are able to be estimated to a reasonable level of accuracy. When the flexible substrate 72 having the array elements therein is applied to a known surface geometry, it is possible to project the array footprint onto the known surface geometry to determine, with reasonable accuracy, element location estimates.

Yet, there are times in which positions for the array element locations are unknown or along changing surface geometry. Several attempts have been made at automatic element location refinement or determination, using known reflectors, maximizing image contrast, or a secondary measuring device, but each comes with its own set of complications.

Thus, there remains a need for methods and algorithms that provide a reasonable level of accuracy on positions of array elements such that the resulting image quality may approach the highest image quality obtainable from accurate knowledge of the positions of the array elements.

SUMMARY OF THE INVENTION

The present invention overcomes the foregoing problems and other shortcomings, drawbacks, and challenges of reconstructing images when positions of the array element locations are unknown or changing. While the invention will be described in connection with certain embodiments, it will be understood that the invention is not limited to these embodiments. To the contrary, this invention includes all alternatives, modifications, and equivalents as may be included within the spirit and scope of the present invention.

According to embodiments of the present invention, a method for locating a plurality of elements comprising a flexible ultrasound phased array includes constructing a matrix of traveltimes by iteratively transmitting a signal from one element of the plurality and receiving the signal at each of the other elements of the plurality. Traveltimes are derived from each received signal and arrayed in a matrix. Relative positions of the first element of the plurality and the last element of the plurality are established and the locations of the remaining elements of the plurality are iteratively modeled to fit the matrix of traveltimes.

One aspect of this embodiment of the present invention utilizes signals derived from bulk waves by minimizing an object function:

$$o = \frac{1}{2} \sum_{R=1}^{N_R} \sum_{T=1}^{N_T} e_{RT}^2,$$

where R is a receiver array element index, T is a transmitter index, and e is a difference between the squared length of the path and a distance between the positions of the transmitter and receiver. The object function may, in some embodiments, be minimized using a gradient-based optimization scheme. A length between a transmitting element and a receiving element may be determined:

$$l = \sqrt{(x_T - x_R)^2 + (y_T - y_R)^2}.$$

One aspect of this embodiment of the present invention utilizes signals derived from bulk waves and signals derived from interface waves by minimizing an object function:

$$o = \frac{1}{2} \sum_{R=1}^{N_R} \sum_{T=1}^{N_T} (e_{RT}^b)^2 + \frac{1}{2} \sum_{R=1}^{N_R} \sum_{T=1}^{N_T} (e_{RT}^i)^2,$$

where R is a receiver array element index, T is a transmitter index, b is bulk wave datasets and lengths, i is interface datasets and lengths, and e is a difference between the squared length of the path and a distance between the positions of the transmitter and receiver. The object function may, in some embodiments, be minimized using a gradient-based optimization scheme. A length between a transmitting element and a receiving element may be determined:

$$l = \int_{s_T}^{s_R} \sqrt{\left(\frac{dx}{ds}\right)^2 + \left(\frac{dy}{ds}\right)^2} \, ds,$$

where s is a coordinate defining a location along a parametric curve.

Other embodiments of the present invention include constructing an ultrasound image by locating a plurality of elements comprising a flexible ultrasound phased array. Locating the plurality of elements includes constructing a matrix of traveltimes by iteratively transmitting a signal from one element of the plurality and receiving the signal at each of the other elements of the plurality. Traveltimes are derived from each received signals and arrayed in a matrix. Relative positions of the first element of the plurality and the last element of the plurality are established and the locations of the remaining elements of the plurality are iteratively modeled to fit the matrix of traveltimes. The modeled locations of the elements may then be used to construct the ultrasound image.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the present invention and, together with a general description of the invention given above, and the detailed description of the embodiments given below, serve to explain the principles of the present invention.

FIGS. 13A, 13B, and 13C are reconstructed images of the sample of FIG. 10A, wherein FIG. 13A is reconstructed with true array geometry, FIG. 13B is reconstructed from a flat, linear array geometry, and FIG. 13C is reconstructed with an array geometry having positions of elements calculated in accordance with an embodiment of the present invention.

FIGS. 16A, 16B, and 16C are reconstructed images of the sample of FIG. 10B, wherein FIG. 16A is reconstructed with true array geometry, FIG. 16B is reconstructed from a flat, linear array geometry, and FIG. 16C is reconstructed with an array geometry having positions of elements calculated in accordance with an embodiment of the present invention.

FIGS. 26A, 26B, and 26C are reconstructed images of the sample of FIG. 24, wherein FIG. 26A is reconstructed with true array geometry, FIG. 26B is reconstructed from an incorrect (flat, linear) array geometry, and FIG. 26C is reconstructed with an array geometry having positions of elements calculated in accordance with an embodiment of the present invention It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

Figure 5:
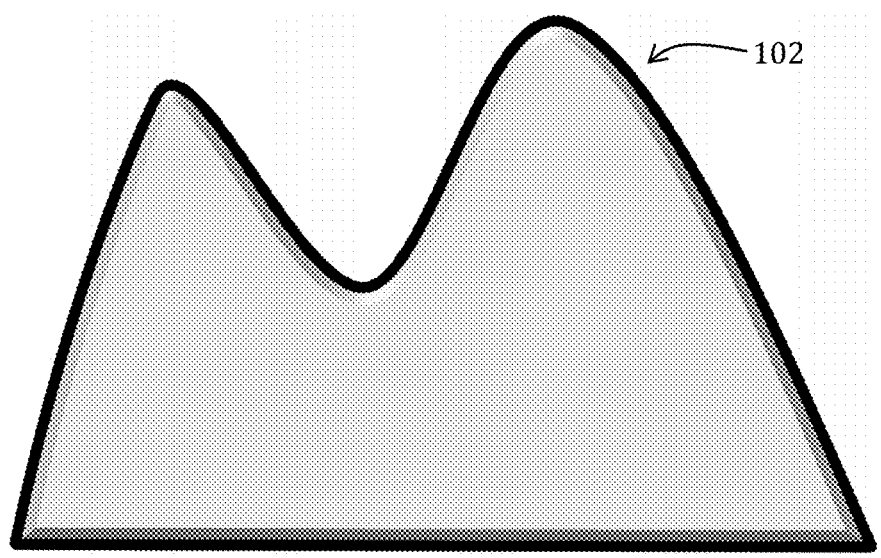
FIG. 5 is a schematic representation of an exemplary non-flat, complex surface used in describing a method of estimating positions of array element locations placed thereon.
Figure 6:
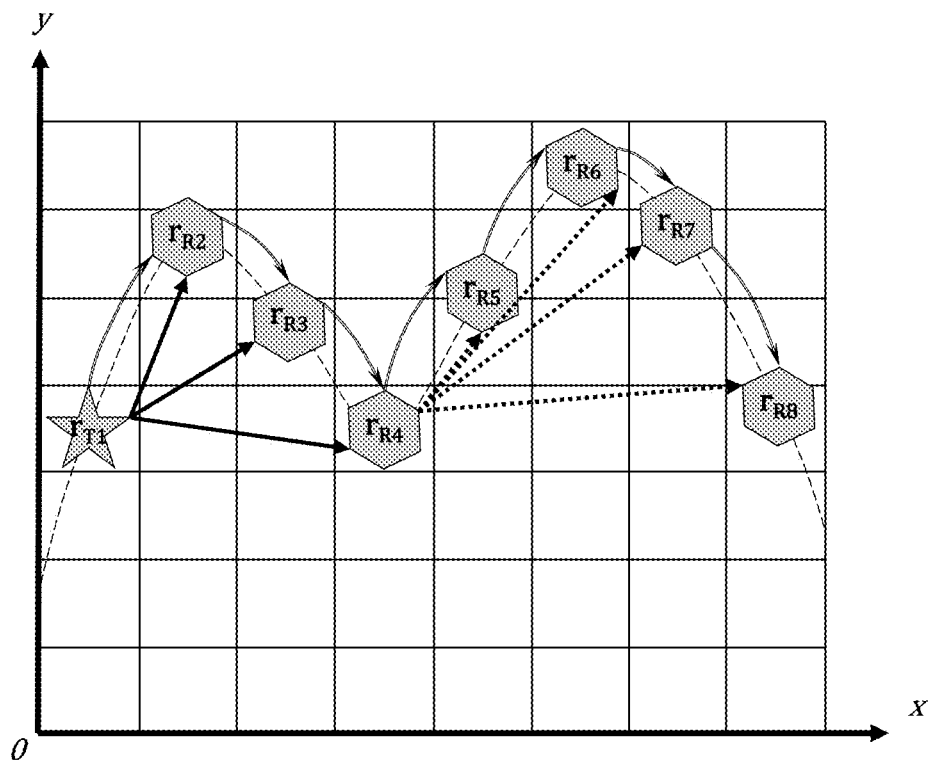
FIG. 6 is a graphical view of an array surface of the exemplary, non-flat, complex surface shown in FIG. 5.
Figure 7:
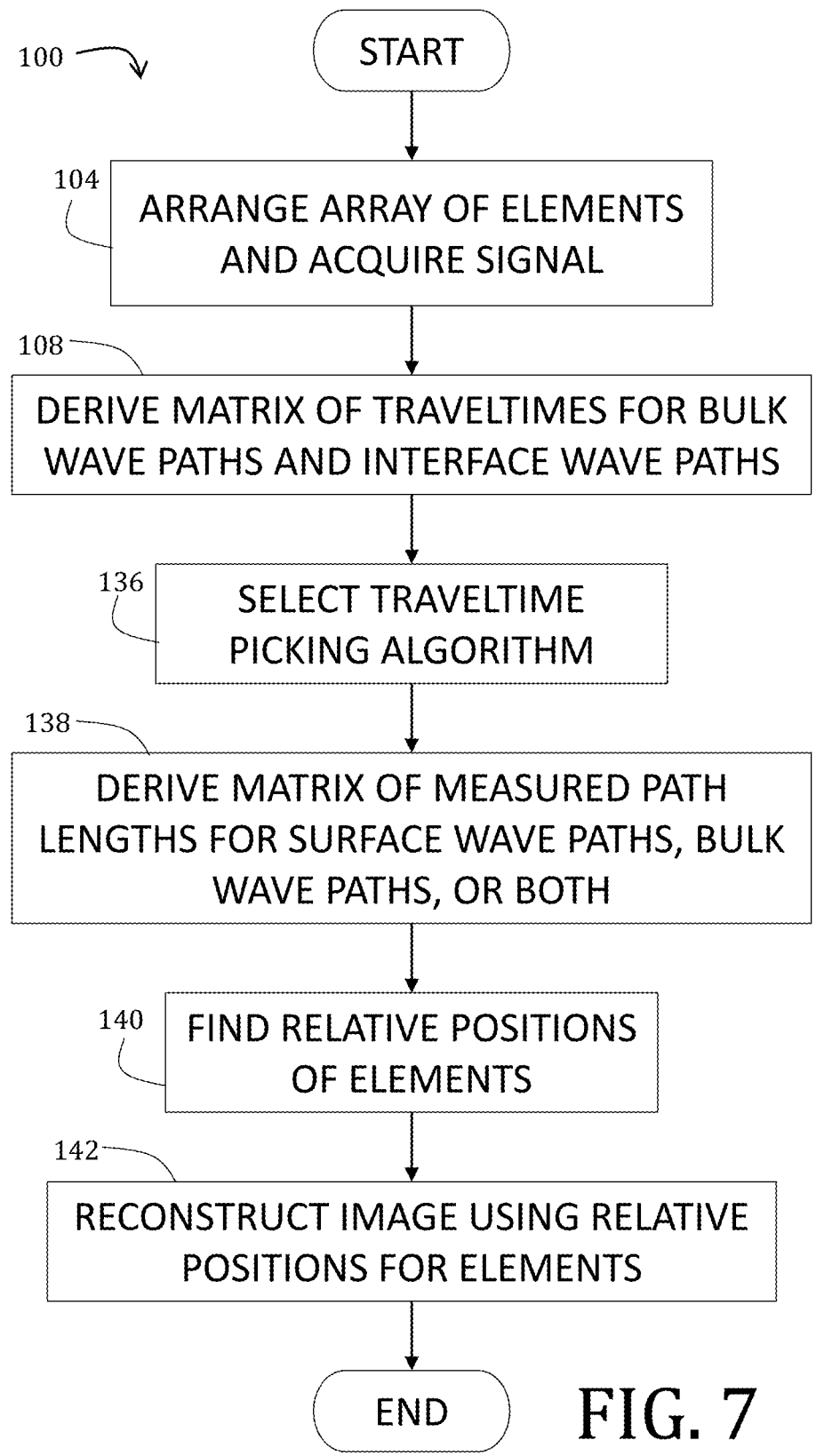
FIG. 7 is a flowchart illustrating a method of estimating positions of array element locations and reconstructing an image therewith in accordance with an embodiment of the present invention.

Referring now to the figures, and in particular to FIGS. 5-7, a method 100 for locating elements of a flexible ultrasound phased array and reconstructing an image therefrom according to an embodiment of the present invention is shown. For purposes of illustration, a non-flat, complex surface 102 and corresponding, exemplary array surface (dashed line) are shown in FIGS. 5 and 6, respectively. For example, the complex surface 102 may have any shape or size and may include undulating or uneven features. FIG. 6 also illustrates and exemplary distribution of elements (i.e., transducers illustrated as a star and hexagons) of the array on the array surface (dashed line) (Block 104). Each element may be a piezoelectric crystal, piezoelectric ceramic, piezoelectric thin films such as poled PVDF polymer elements, piezoelectric micromachined ultrasonic transducers (PMUT), electrostatic elements such as capacitive micromachined ultrasonic transducers (CMUT), electromagnetic acoustic transducers (EMAT), and so forth. A first element, $r_{T1}$ (illustrated as the star), may be configured to act as a transmitter and receiver while other elements, $r_{R2}$, $r_{R3}$, $r_{R4}$, $r_{R5}$, $r_{R6}$, $r_{R7}$, $r_{R8}$ (illustrated as the hexagons), may be configured to act as receivers.

Given the arrangement of the array of elements of FIG. 6, several types of wave paths (i.e., rays) between the transmitter and each receiver may exist. Given a homogenous wave speed, arrival times (i.e., "traveltimes") of wave packets vary due to the differing path lengths. Bulk wave paths (illustrated with thick lined arrows) may include those direct, straight-line paths connecting the transmitter $r_{T1}$ to each receiver whose path is unobstructed (in FIG. 6 this includes $r_{R2}$, $r_{R3}$, $r_{R4}$, $r_{R5}$, $r_{R6}$, $r_{R7}$, $r_{R8}$). Interface wave paths (thin lined arrows) propagate along the curved array surface between elements. Keller diffracted waves, which are a combination of surface waves and bulk waves, are also shown (dotted line arrows). Each wave path (bulk waves, interface waves, and Keller diffracted waves) encodes some information about the array surface.

With the array of elements set, sound waves may be transmitted from the transmitter and received at all elements (including the transmitter) (FIG. 7, Block 104). Generally, software configured to automate the array may cause one element of the array (the transmitter) to be activated. When activation occurs, a signal is sent from the software to an array controller (one exemplary model being a TPAC Pioneer 64/64 FMC). The array controller selects the one element to be the transmitter and activates the transmitter by transmitting (or firing) an electrical pulse. A shape of the electrical pulse waveform may vary (square, spike, etc.) and may depend on the manufacturer and the particular application. The electrical pulse causes the transmitter piezoelectric crystal of the element to vibrate. A boundary vibration of a surface of the element causes a wave to propagate away from the element, through any coupling layers that may be associated with a housing or a packaging and into the domain to be imaged. At an interface between the array of elements and the domain to be imaged, interface and bulk wave types are produced as described above. Again, these multiple wave types propagate at different speeds, and each wave type will have an expanding wavefront. Some incident waves may be reflected by boundaries or defects within the domain; other incident waves may travel directly from the transmitter to receivers along direct bulk or interface wave paths. Received waves cause the receiver piezoelectric crystal to vibrate. Because the elements are electromechanically coupled, vibrations of the piezoelectric crystal cause an electrical signal to be produced, which is transmitted to and recorded by the array control. The electrical signal may also be digitally streamed back to the software. When a single, still image is desired, the process occurs once and the received signal data is reconstructed to form a picture. Other times, received data is continuously streamed and interlaced with an imaging algorithm to reconstruct a series of images resulting in a near real-time video.

With data acquired, and using a computer system 106, a matrix of traveltimes, T, linking all transmitters (columns) and receivers (rows), i.e., an FMC dataset, may be derived from the received signals for all direct bulk wave paths and interface wave paths (Block 108, FIG. 7). Details of the computing system 106 suitable for processing the acquired data in accordance with an embodiment of the present invention is described with reference to FIG. 8. The illustrative computing system 106 may be considered to represent any type of computer, computer system, computing system, server, disk array, or programmable device such as multi-user computers, single-user computers, handheld devices, networked devices, or embedded devices, etc. The computing system 106 may be implemented with one or more networked computers 110 using one or more networks 112, e.g., in a cluster or other distributed computing system through a network interface 114 (illustrated as "NETWORK I/F"). The computing system 106 will be referred to as "computer" for brevity's sake, although it should be appreciated that the term "computing system" may also include other suitable programmable electronic devices consistent with embodiments of the invention.

The computer 106 typically includes at least one processing unit 116 (illustrated as "CPU") coupled to a memory 118 along with several different types of peripheral devices, e.g., a mass storage device 120 with one or more databases 122, an input/output interface 124 (illustrated as "I/O I/F") coupled to a user input 126 and a display 128, and the network interface 114. The memory 118 may include dynamic random access memory ("DRAM"), static random access memory ("SRAM"), non-volatile random access memory ("NVRAM"), persistent memory, flash memory, at least one hard disk drive, and/or another digital storage medium. The mass storage device 120 is typically at least one hard disk drive and may be located externally to the computer 106, such as in a separate enclosure or in one or more networked computers 110, one or more networked storage devices (including, for example, a tape or optical drive), and/or one or more other networked devices (including, for example, a server 130).

The processing unit 116 may be, in various embodiments, a single-thread, multi-threaded, multi-core, and/or multi-element processing unit (not shown) as is well known in the art. In alternative embodiments, the computer 106 may include a plurality of processing units that may include single-thread processing units, multi-threaded processing units, multi-core processing units, multi-element processing units, and/or combinations thereof as is well known in the art. Similarly, the memory 118 may include one or more levels of data, instruction, and/or combination caches, with caches serving the individual processing unit or multiple processing units (not shown) as is well known in the art.

The memory 118 of the computer 106 may include one or more applications 132 (illustrated as "APP."), or other software program, which are configured to execute in combination with the operating system 134 (illustrated as "OS") and automatically perform tasks necessary for performing the method of FIG. 7, with or without accessing further information or data from the database(s) 122 of the mass storage device 120.

Figure 8:
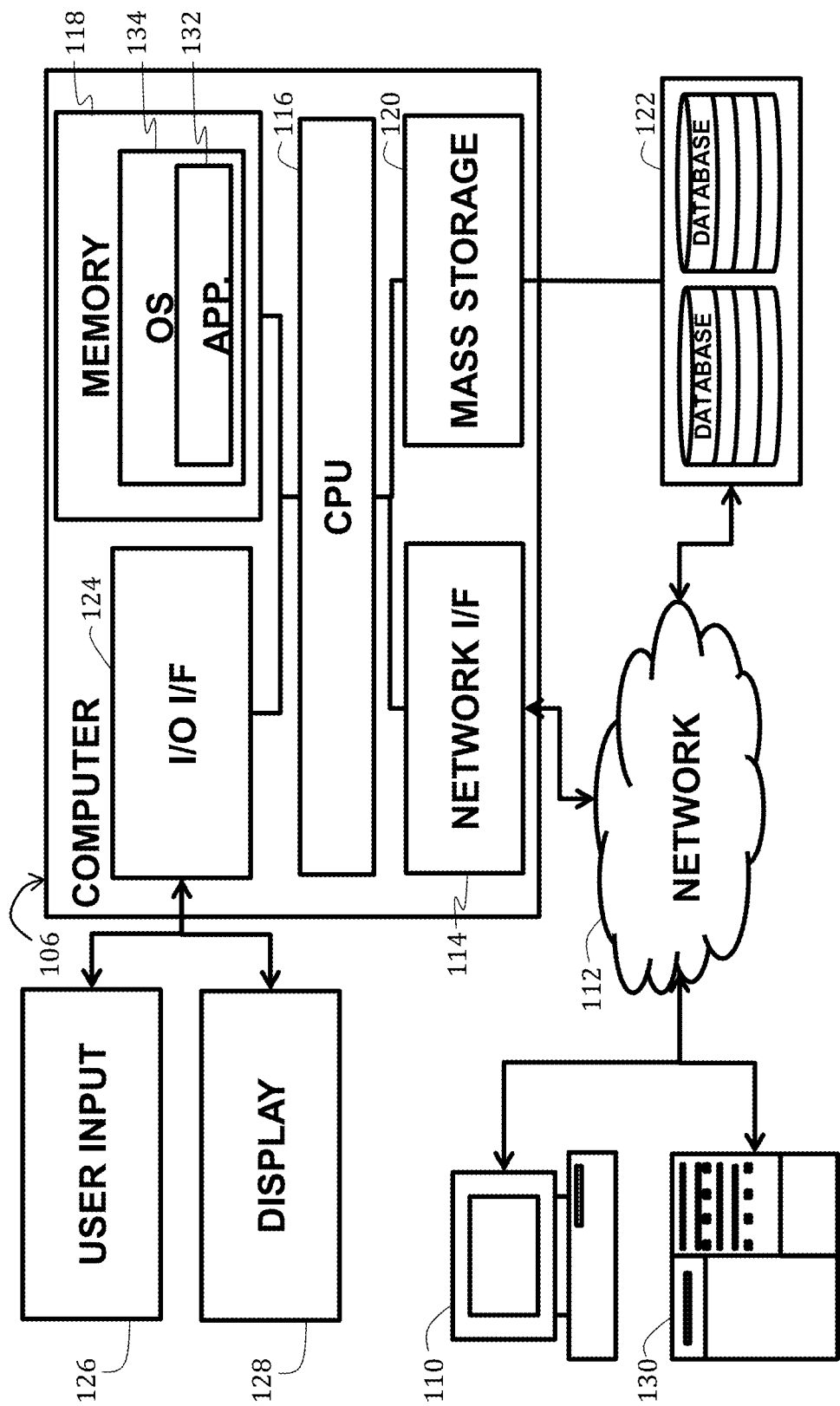
FIG. 8 is a schematic view of a computer suitable for use with embodiments of the present invention.

Those skilled in the art will recognize that the environment illustrated in FIG. 8 is not intended to limit the present invention. Indeed, those skilled in the art will recognize that other alternative hardware and/or software environments may be used without departing from the scope of the invention.

Referring now again to FIG. 7, the method continues and includes selecting a traveltime-picking algorithm (Block136). Suitable traveltime picking algorithms may include, for example, the Akaike Information Criterion (AIC), cross-correlation algorithm (see, R. SLEEMAN et al., "Robust automatic P-phase picking: an on-line implementation in the analysis of broadband seismogram recordings," *Physics of the Earth and Planetary Interiors*, Vol. 113 (1999)), or instantaneous frequency methods (see, C. SARAGIOTIS et al., "Automatic traveltime-picking using the instantaneous traveltime," *Geophysics*, Vol. 78 (2013)).

Presuming that for regions near the array the wave speed, c, is homogenous, measured path lengths along either surface wave paths or bulk wave paths may be found (Block 138):

$$L^d = cT. \tag{3}$$

Wave path length data may then be used to find relative positions of the elements of the array. Absolute positions of the elements are not necessary as imaging accuracy depends only on relative positions. Reflection, rotations, or translations in the relative position of the overall shape of the array will result in corresponding reflection, rotation, or translation in a resulting image. Reflections, rotations, translations, and combinations thereof may come about due to the nonuniqueness of the element position solution (i.e., multiple array position combinations that will produce the same traveltime matrix, T).

According to one embodiment of the present invention, finding the relative positions of the elements includes inputting a distance along a bulk wave path between any two elements of the array having known locations, which may be written as:

$$l = \sqrt{(x_T - x_R)^2 + (y_T - y_R)^2} \tag{4}$$

where $\{x_T, y_T\}^t$ and $\{x_R, y_R\}^t$ are the positions of a transmitter and receiver, respectively. A less constrictive relationship can be defined by:

$$e = l^2 - (x_T - x_R)^2 - (y_T - y_R)^2, \tag{5}$$

where e is a difference between the squared length of the path and a distance between the positions of the transmitter and receiver. When the transmitter and receivers are at proper positions, the value of e will be zero. An optimization problem may be formed by prescribing an objective function that links traveltimes to the element positions in a similar way. The error between the measured path length and two relative array positions may be written as:

$$e_{RT} = (L_{RT}^d)^2 - (L_{RT}^s)^2, \tag{6}$$

with receiver array element index, R, transmitter index, T, element of the path length dataset matrix, $L_{RT}^d$, and element of the synthetic path length matrix, $L_{RT}^s$. A synthetic path length matrix may be calculated from the estimated element locations through a model. According to one embodiment of the present invention, the model is the analytical expression given in Eq. (4). A corresponding objective function may then be defined as one-half of the sum of the squared errors and is written as:

$$o = \frac{1}{2} \sum_{R=1}^{N_R} \sum_{T=1}^{N_T} e_{RT}^2. \tag{7}$$

By minimizing the objective function, a difference between measured and synthetic squared path lengths is driven to zero. A gradient-based optimization scheme may be used, provided that a proper set of gradients (i.e., differentials of the object function with respect to each of the array coordinates) may be obtained. Possible gradient based optimizations schemes may include: Steepest Descent, Conjugate Gradient, Broyden-Fletcher-Goldfarb-Shanno ("BFGS") methods, etc. General gradients may be written using the chain rule on the object function, as it is a function of the squared errors of the synthetic model and measured data. Another possibility for wave paths requiring more complex numerical modeling may include an adjoint method of finding gradients.

When considering only bulk waves in a curved transducer array of unknown profile curvature, multiple wave paths will cross through the acoustic medium near the array and may give a sufficient set of information from which to determine the relative array element positions. Difference between the squared measured wave path lengths and those of the analytical model may be written:

$$e_{RT}^b = (L_{RT}^b)^2 - (x_T - x_R)^2 - (y_T - y_R)^2. \tag{8}$$

The superscript, b, indicates straight ray bulk path lengths. Differentiating Eq. (7) with respect to the transmitter coordinates yields:

$$\frac{do}{dx_T} = \frac{1}{2} \sum_{R=1}^{N_R} \frac{do}{de_{RT}^b} \frac{de_{RT}^b}{dx_T} = -2 \sum_{R=1}^{N_R} e_{RT}^b (x_T - x_R), \tag{9}$$

$$\frac{do}{dy_T} = \frac{1}{2} \sum_{R=1}^{N_R} \frac{do}{de_{RT}^b} \frac{de_{RT}^b}{dy_T} = -2 \sum_{R=1}^{N_R} e_{RT}^b (y_T - y_R), \tag{10}$$

which are the gradients for each transmitter location. Because the data matrix is composed of traveltimes between all pairs of transmitters and receivers, and all elements of the array have a turn acting as the transmitter, optimization of either transmitter or receiver position is arbitrary.

Figure 9:
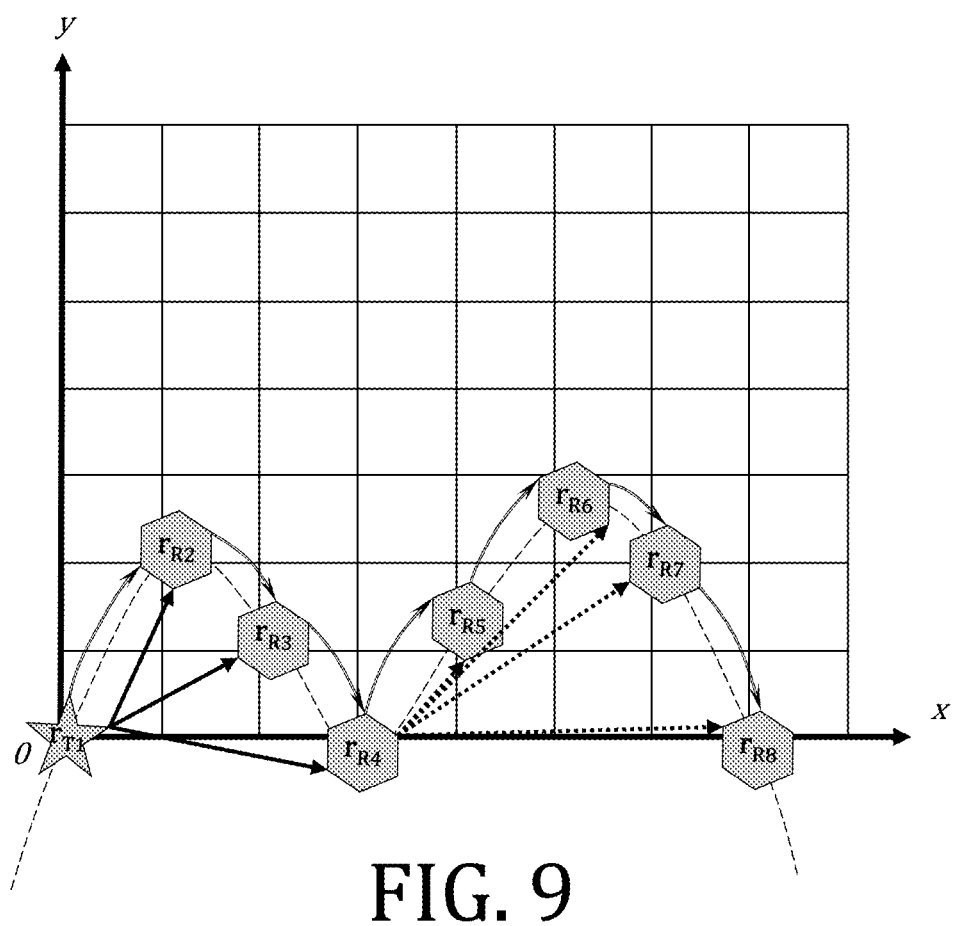
FIG. 9 is the Cartesian coordinate model of the linear array of elements with a position of the first element being constrained to (0,0) and the y-coordinate of the last element position being constrained to zero.

Since no element location is known, a first element position may be set to (0,0) and, the last element's y-position may be constrained to zero (see FIG. 9). Constraining the first element locks the optimization in space so that the elements do not translate off to infinity; fixing the second array vertical position constrains rotation. All other coordinates may then be determined by an optimization algorithm (Block 140). The BFGS algorithm may act as the testbed optimization code. All other array coordinates are initialized to random numbers drawn from the normal distribution between −1 and 1.

Once adequate estimates of the location of each element of the array are obtained, the estimated locations (coordinates) may be used directly in the TFM-FMC procedure outlined in Eq. (1) and Eq. (2). According to some embodiments, cascade plots may be used to graphically represent portions of the FMC dataset (i.e., the block of all signals acquired from $r_T$ and received at a particular $r_R$ location). The complete dataset of $N_T$ transmitter locations, $N_R$ receiver locations, and $N_t$ time points is a three-dimensional array of discrete time domain signals. Each signal would be subsequently processed via the traveltime-picking algorithm to find the onset of the pulse of interest (whether arising from the bulk or interface paths).

Another embodiment of the present invention is directed to a method of locating elements of a flexible ultrasound phased array and reconstructing an image therefrom that utilizes both bulk and interface waves. The embodiment described above implements an array element-finding algorithm to explicitly define a set of discrete x and y coordinates based on bulk waves. To incorporate interface wave information, parametric curves are used: x(a, s) and y(b, s), where a and b are parameter vectors, and s is a coordinate defining a location along each parametric curve. Incorporating interface waves into the calculation provides a benefit of including information regarding distances between pairs of elements of the array along the array surface, regardless of profile. Such additional information improves the array element spacing reconstruction.

A new formulation of the objective function, o, may be written to include the errors of bulk wave paths $e_{RT}^b$ and interface wave paths $e_{RT}^i$:

$$o = \frac{1}{2}\sum_{R=1}^{N_R}\sum_{T=1}^{N_T}(e_{RT}^b)^2 + \frac{1}{2}\sum_{R=1}^{N_R}\sum_{T=1}^{N_T}(e_{RT}^i)^2, \qquad (11)$$

which keeps the same form as the previous objective function, Eq. (7). The errors between the measured path length and two relative array positions may be written as:

$$e_{RT}^b = (L_{RT}^{bd})^2 - (L_{RT}^{bs})^2, \qquad (12)$$

$$e_{RT}^i = (L_{RT}^{id})^2 - (L_{RT}^{is})^2, \qquad (13)$$

where $L_{RT}^{bd}$ and $L_{RT}^{id}$ are true bulk and interface datasets of lengths, and $L_{RT}^{bs}$ and $L_{RT}^{is}$ are synthetic bulk and interface lengths resulting from the model. For bulk waves, a straight line between two points may still be used as an analytical model, as given in Eq. (4); however, when parameterizations x(a, s) and y(b, s) are substituted, then Eq. (4) becomes a function of a, b, and s. Gradients with respect to the coordinate, s, and general set of parameters, a and b, may then be written as $$\frac{do}{ds}, \frac{do}{da_j}, \text{ and } \frac{do}{db_j}.$$

These may be found using a chain rule just as in the bulk wave only derivations.

The simplicity of the model for the bulk wave path, Eq. (4), is lost when considering the interface waves that propagate along the likely curved path of the flexible array interface and interrogated media. The general expression for length along a path is now written as:

$$l = \int_{s_T}^{s_R}\sqrt{\left(\frac{dx}{ds}\right)^2 + \left(\frac{dy}{ds}\right)^2}\,ds, \qquad (14)$$

which serves as the analytical model for propagation along the interface. Thus, the error between the dataset and analytical model may be written as:

$$e_{RT}^i = (L_{RT}^{id})^2 - \left(\int_{s_T}^{s_R}\sqrt{\left(\frac{dx}{ds}\right)^2 + \left(\frac{dy}{ds}\right)^2}\,ds\right)^2. \qquad (15)$$

One difficulty with the interface wave formulation is that the integral, depending on the chosen parameterization, must be evaluated numerically. For example, the steps/intervals along the location coordinate, s, may be made arbitrarily small, thus providing acceptable accuracy. It should be noted that derivative and integral operations are interchangeable for constant limits of integration (i.e., Leibniz integral rule), and thus the objective function derivatives (Eq. (11)) depending on the interface wave errors may be found.

Using Eqs. (16) and (17), a gradient-based optimization scheme may be devised. The method according to this embodiment of the present invention still requires that parameterizations $x(a, s_1)=0$, $y(b, s_1)=0$, and $y(b, s_{N_T})=0$, or other equivalent conditions. The usefulness of including the interface waves is that the path between a transmitter and receiver is not obstructed along the interface; however, some bulk wave paths may be obstructed due to significant deformation of the array surface or a significant scatterer located proximate to the array. Such deformations or scatterers would lead to a reduced amount of accurate bulk wave data that may be compensated for using the interface wave data. Furthermore, interface waves contain extremely accurate information about element spacing. Moreover, some of the more recent experimental flexible arrays do not necessarily assume that the array elements maintain a constant spacing, and thus it is important to have this information in those cases.

While no a priori knowledge of the surface profile or internal defects is assumed in the embodiments of the present invention described above, another embodiment of the present invention may incorporate such information. For example, constraints may be added to either embodiment described above by way of Lagrangian multipliers. As such, constraint terms are appended to the objective functions (Eq. (7) of the bulk wave embodiment or Eq. (11) of the bulk and interface wave embodiment). One of ordinary skill in the art would readily appreciate the manner by which such constraints may be incorporated.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

Example 1—Experimental Tests of the Bulk Wave Only Algorithm

An ultrasound system for testing samples included a phased array probe (Olympus XACT-10036) having 64 elements and 5 MHz center frequency, an array controller (Pioneer 64/64 full matrix capture by The Phase Array Company), and a computer (Alienware Area-51m) configured to acquire data at high speeds.

Figure 10A:
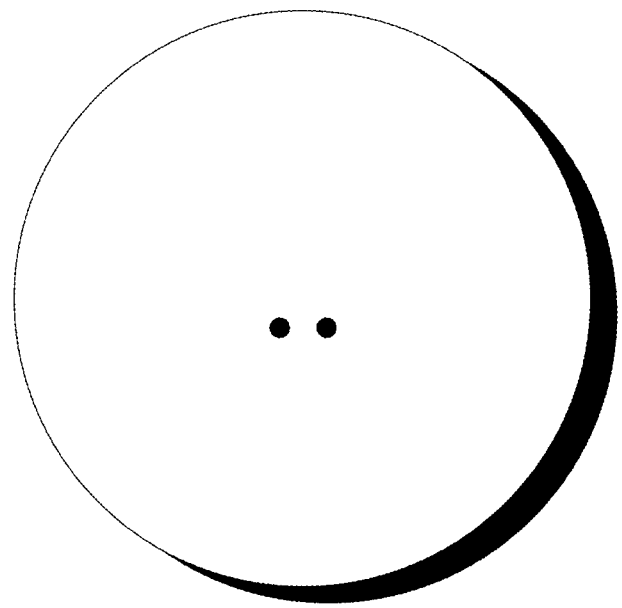
FIGS. 10A and 10B are top views of samples of aluminum discs having hole patterns extending the thickness of each, wherein a pattern in FIG. 10A includes two holes and a pattern in FIG. 10B includes a U-shape/saw tooth shape.

Samples were prepared from 6061 aluminum discs of 3-inch diameter and 1-inch thickness. Hole patterns were drilled into each sample (a pair of holes in FIG. 10A and a U-shape/saw tooth hybrid pattern in FIG. 10B); each hole had a diameter of 2 mm and extended through the thickness of the disc. For purposes of calculations, each disc was presumed to have a Poisson's ratio of 0.33, a Young's modulus of 75.8 GPa, a longitudinal wavespeed of 6449.5 m/s, and a wavelength of 1.24 mm (at 5 MHz).

Figure 1:
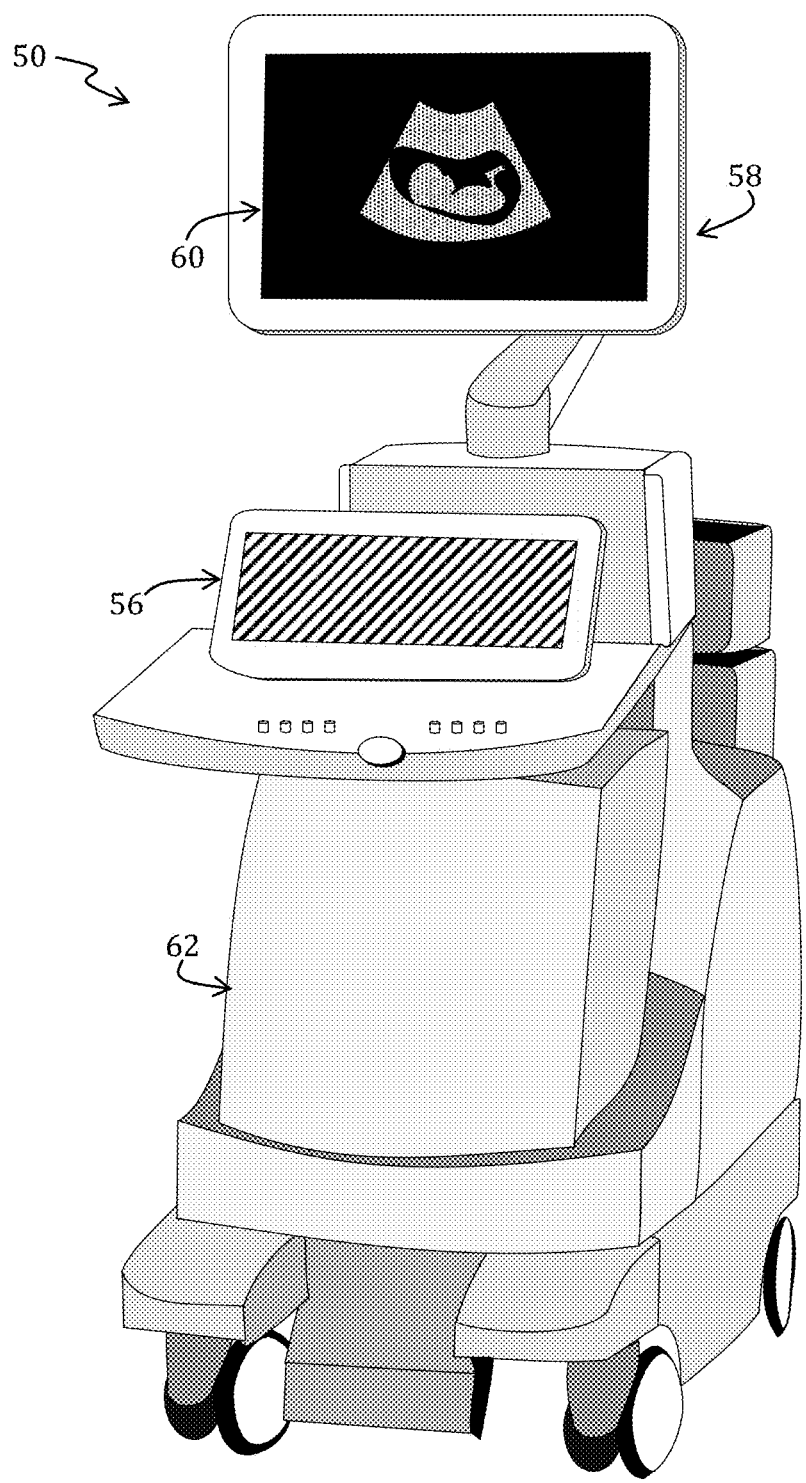
FIG. 1 is a side-elevational view of a conventional sonograph machine suitable for acquiring ultrasound images.
Figure 2A:
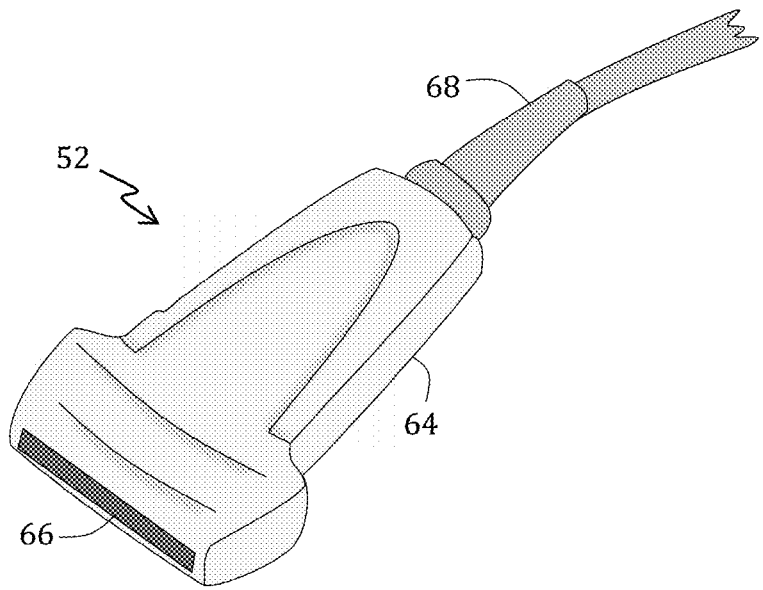
FIGS. 2A and 2B are perspective views of a conventional linear transducer and a conventional flexible transducer, respectively, suitable for use with the sonograph machine of FIG. 1.
Figure 2B:
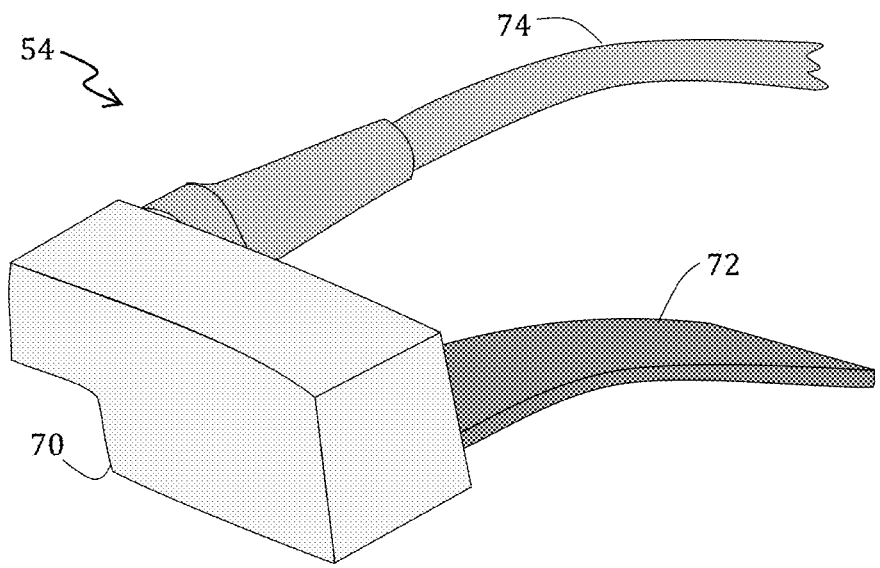
Figure 3:
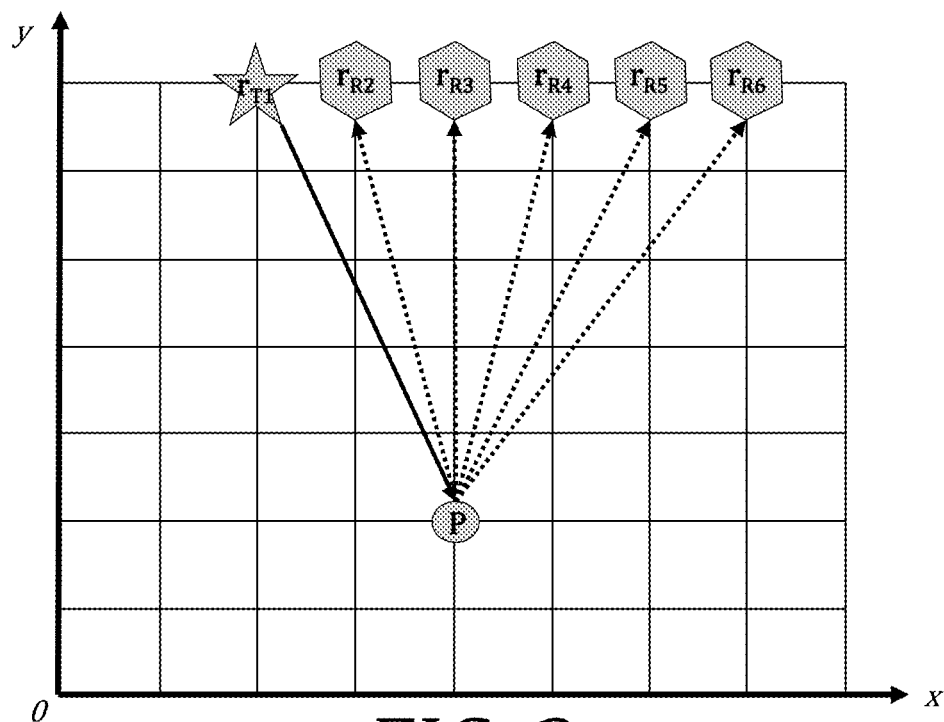
FIG. 3 is a Cartesian coordinate model of a linear array of elements associated with the linear transducer of FIG. 2A.
Figure 4:
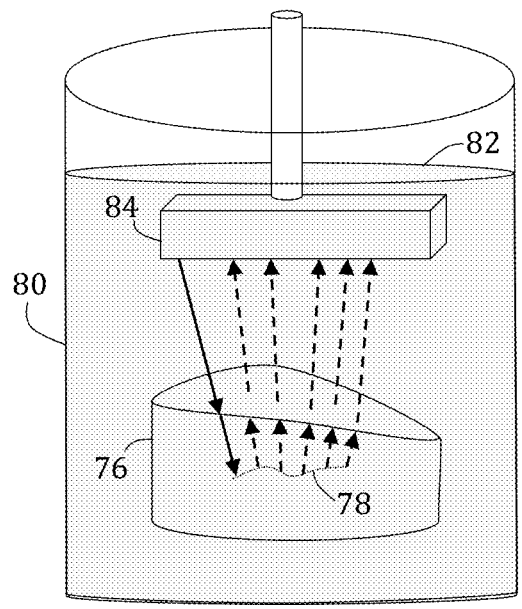
FIG. 4 is a side elevational view of an alternative, conventional method for performing ultrasound imaging on an object having non-flat surfaces by embedding the object in a medium.
Figure 11A:
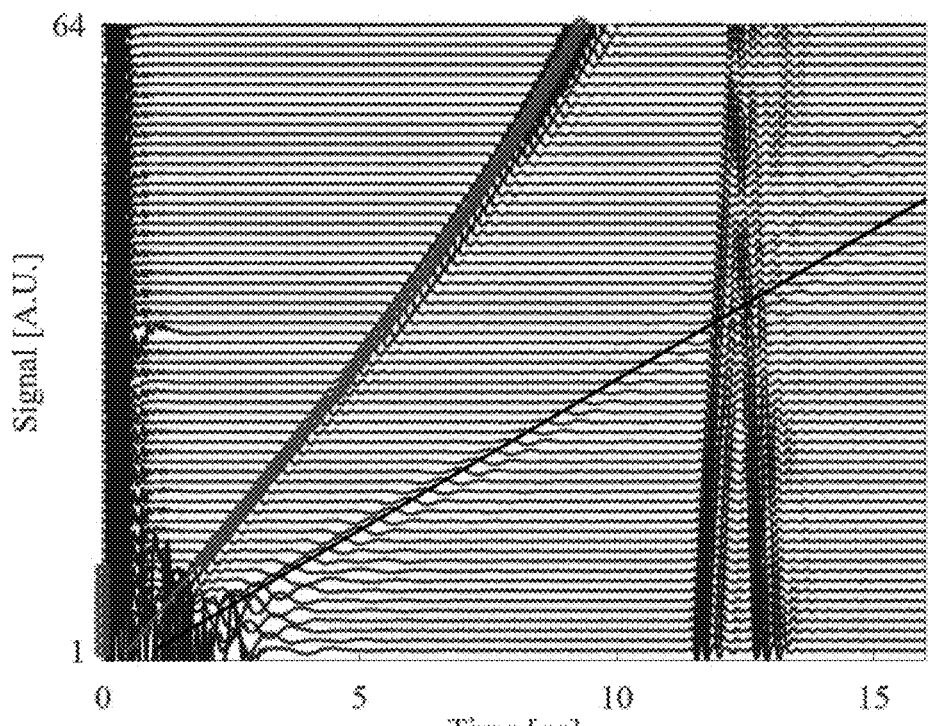
FIGS. 11A and 11B are cascade plots calculated from raw scan data obtained for the first and the $32^{nd}$ transmitters of an array of element scanning the sample of FIG. 10A.
Figure 11B:
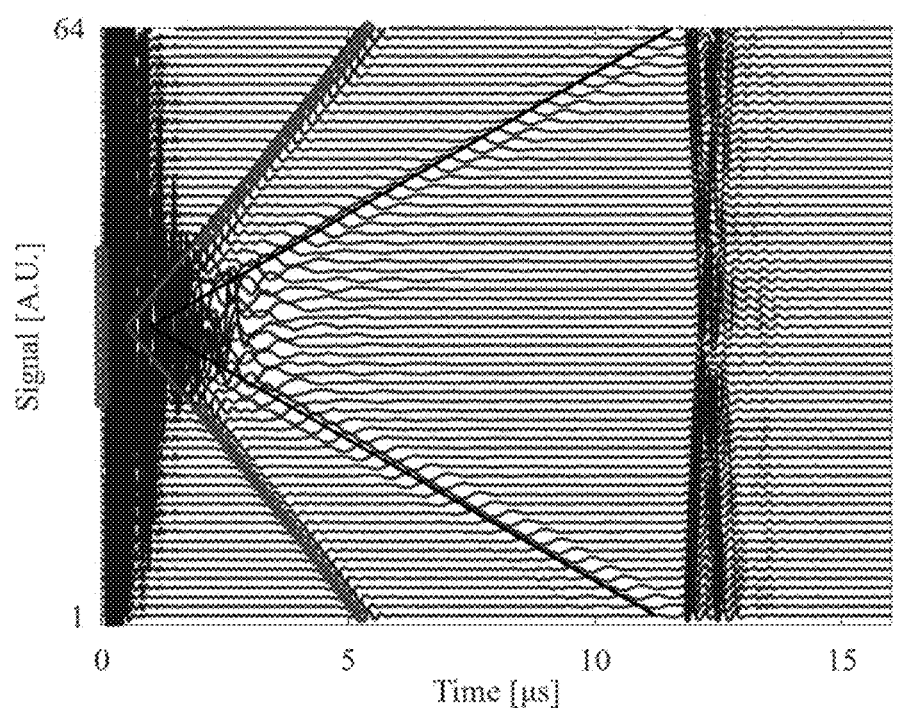

The surface of each sample was scanned with the phased array probe of the ultrasound system (as shown in FIG. 2B). FIGS. 11A and 11B are cascade plots (i.e., a block of received signals normalized and centered on a respective receiver index for a particular transmitter) calculated from raw scan data for a first transmitter and a 32nd transmitter of the phased array, respectively. Within the cascade plots, true longitudinal bulk wave arrivals are indicated by the red line; the black line corresponds to the surface wave arrivals (i.e., Rayleigh wave); red circles are the traveltimes of the bulk waves that have been found by traveltime-picking algorithm, based on a custom cutoff level scheme. The custom cutoff level scheme included zeroing out initial microseconds of data from FIGS. 11A and 11B so as to eliminate "main bang" signal effects (an electrical effect and not a true signal of a mechanical wave). The envelope of the signal is then found by taking the modulus of the Hilbert transform of each signal and a cutoff level was specified (relative to a maximum amplitude of the signal). The time corresponding to the first signal envelope peak found above that cutoff level may be selected as the bulk wave (traveling at the longitudinal wave speed) traveltime, and a dataset of all possible transmission paths (i.e., for each transmitter-receiver combinations) formed the traveltime matrix of FIG. 12A. The cascade plot of FIG. 11A contains data from all receivers when the first array element acts as a transmitter; therefore, the signals of FIG. 11A make up the first column of the traveltime matrix shown in FIG. 12A. To construct the full traveltime dataset, each element of the array takes a turn at transmitting.

The red and black circles do not begin at zero time for the transmitters because the traveltime-picking algorithm utilizes pulse envelope peak rather than pulse envelope onset. Some additional delays may be introduced by the array controller, which may be compensated by a hand-tuned delay that is subtracted from the picked traveltimes. It should also be noticed that there are several traveltimes (red circles) centered about the transmitting element that have a zero traveltime. Traveltimes centered at the transmitting element are zero. For elements proximate to the transmitting element, strong and heavy overlapping pulses due to mechanical effects rendered traveltime-picking based on pulse envelope peak detection impossible. Instead, it was presumed that traveltime from elements proximate to the transmitting elements is the product of the element pitch and wavespeed.

Figure 12A:
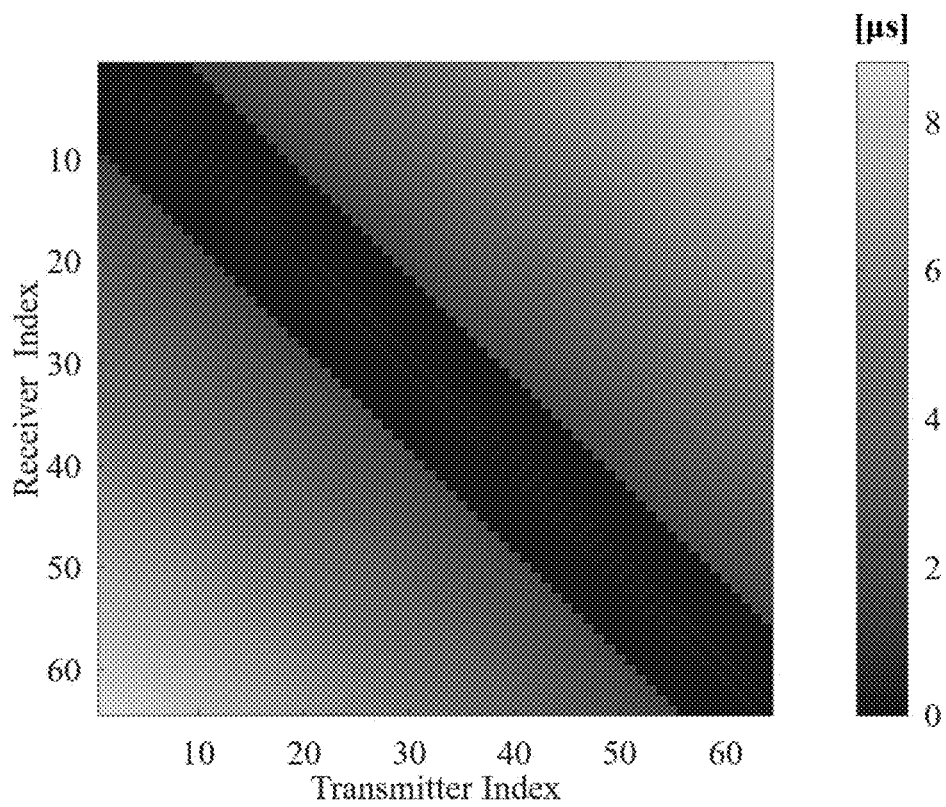
FIGS. 12A and 12B graphically illustrate measured and true traveltime matrices, respectively, from the sample of FIG. 10A.
Figure 12B:
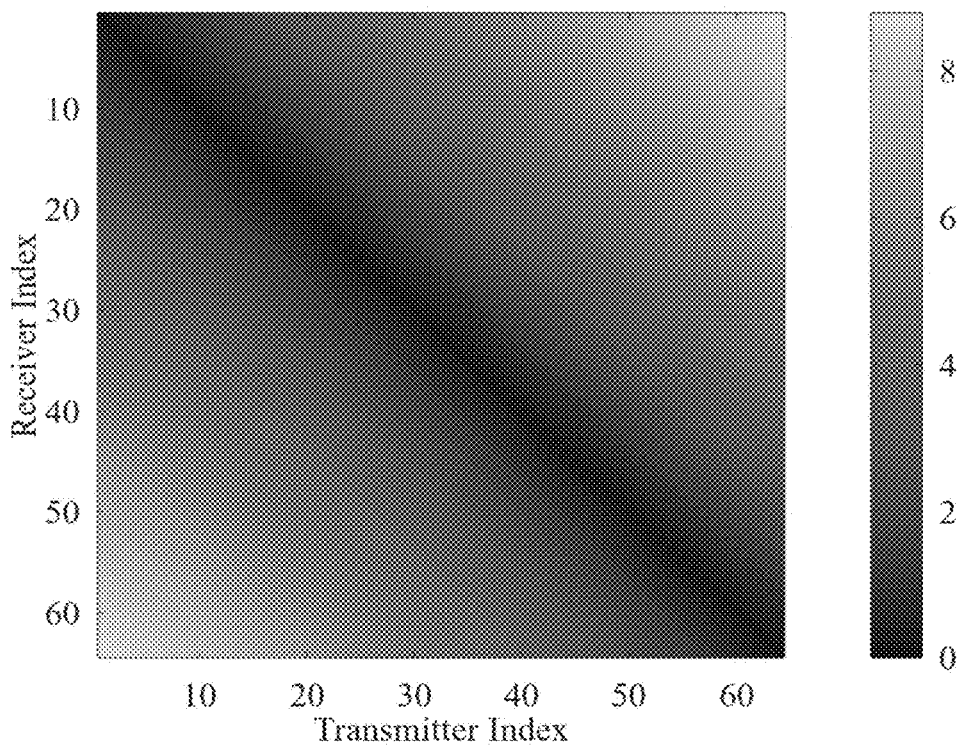

FIGS. 12A and 12B graphically illustrate the measured and true traveltime matrices, respectively, for the hole pair sample. Because traveltimes for those elements proximate to the transmitting element were difficult to determine, the measured traveltime matrix (FIG. 12A) includes a significant band of zero values surrounding the tridiagonal band.

In the array element locating algorithm (as given in Eqs. (7-10)), traveltimes equal to zero do not contribute to the element location. These zero value elements were treated in a manner similar to transmitter-receiver pairs occurring at the same spatial location and thus not included in optimization. This error is, obviously, not observed in the true traveltime matrix (FIG. 12B).

Figure 13A:
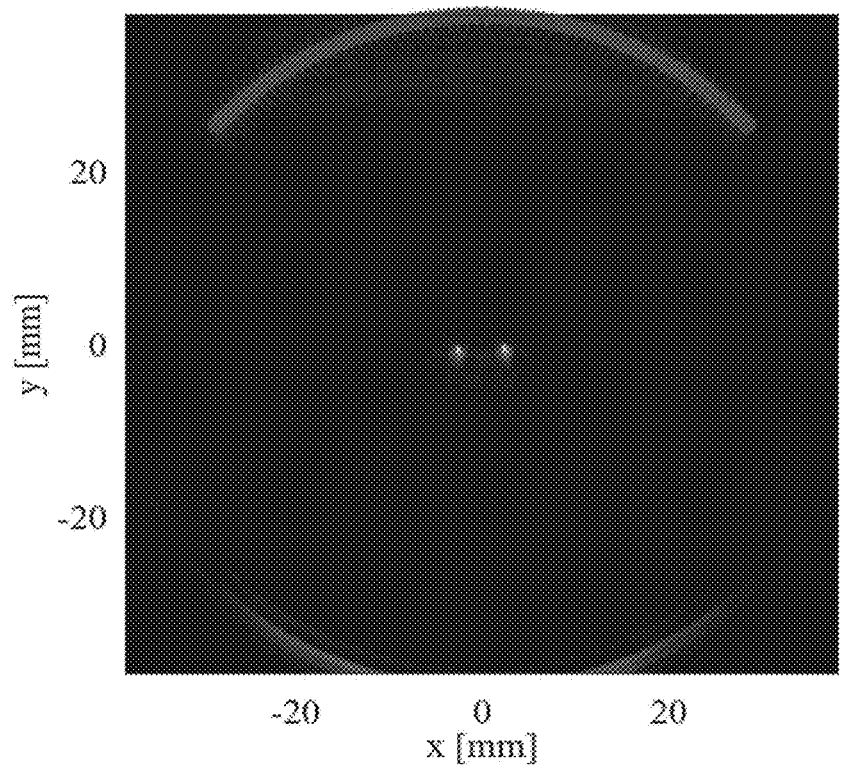
Figure 13B:
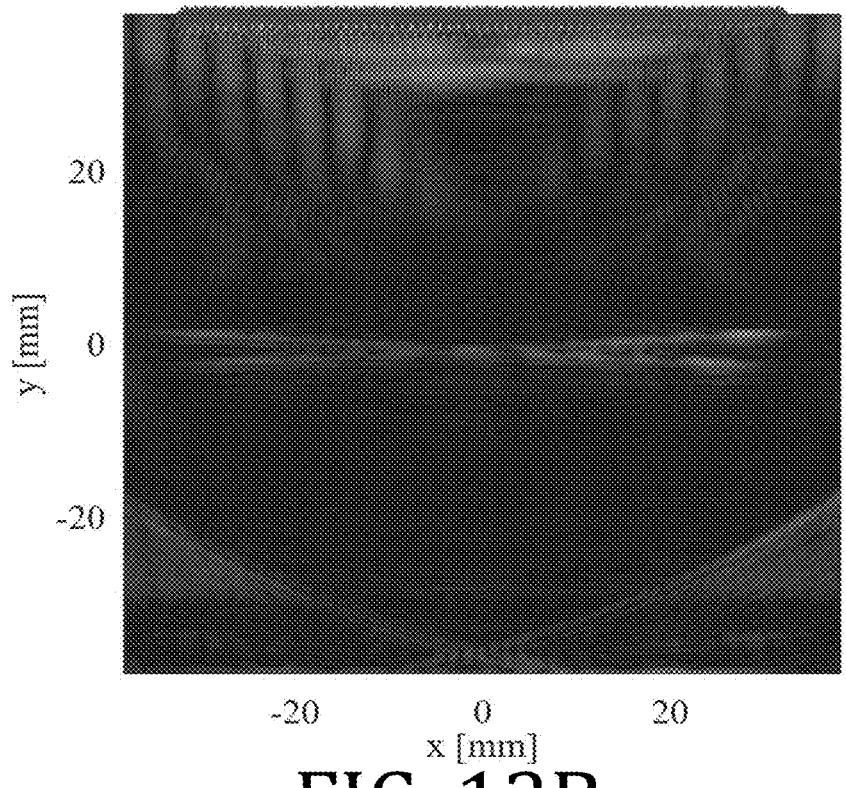
Figure 13C:
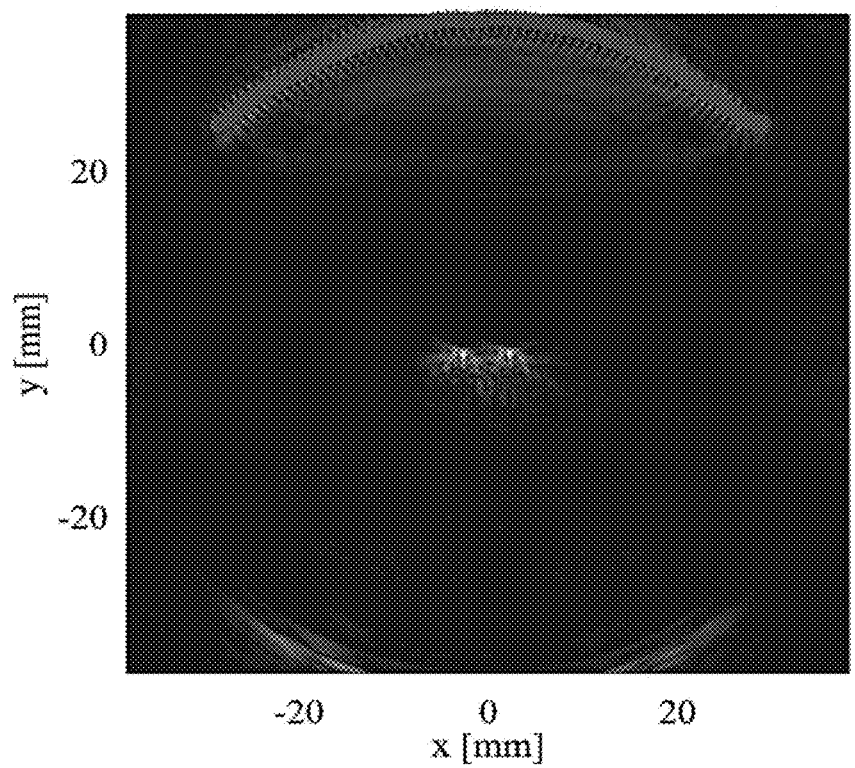

Image reconstruction included TFM using array element locations computed using the true traveltime matrix. In each of FIGS. 13A-13C, element locations are plotted using red circles. FIG. 13A is a high quality image reconstructed with the true array geometry and demonstrates few artifacts (i.e., errors in the image produced by errors in the imaging algorithm parameters, such as the array element positions). FIG. 13B is an image reconstructed with a flat, linear array geometry—here scatterers are completely obscured due to the coordinated errors in the array element locations (i.e., an array with an incorrect overall profile). FIG. 13C is an image reconstructed with the calculated array geometry from measured traveltimes with coordinated dropped data. The image of FIG. 13C demonstrates scatterers positioned at the approximate locations; however, small errors in the reconstructed element locations yielded blurring near the brightest points of the reconstructed scatterers. Table 1, below, provides the mean and standard deviation in differences between the true and estimated array element locations from FIGS. 13A and 13C.

TABLE 1

|  | Mean [m] | Std. Dev. [m] |
| --- | --- | --- |
| x-coordinates | 3.2437e−04 | 8.5216e−05 |
| y-coordinates | −6.7612e−04 | 3.7482e−04 |

Figure 10B:
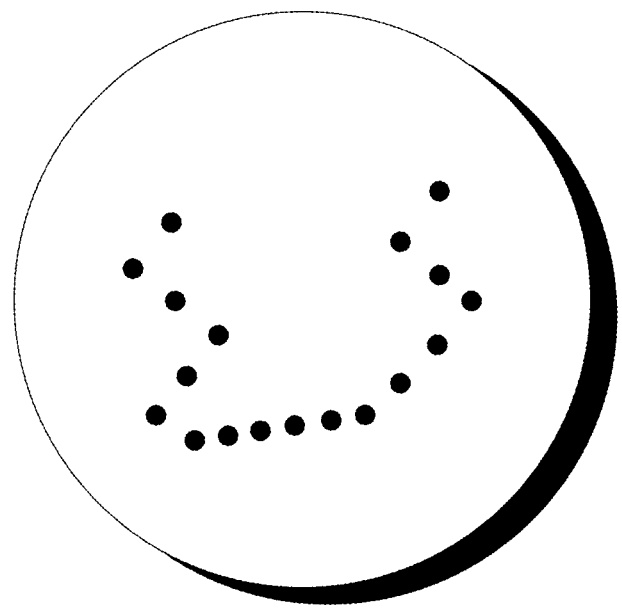
Figure 14A:
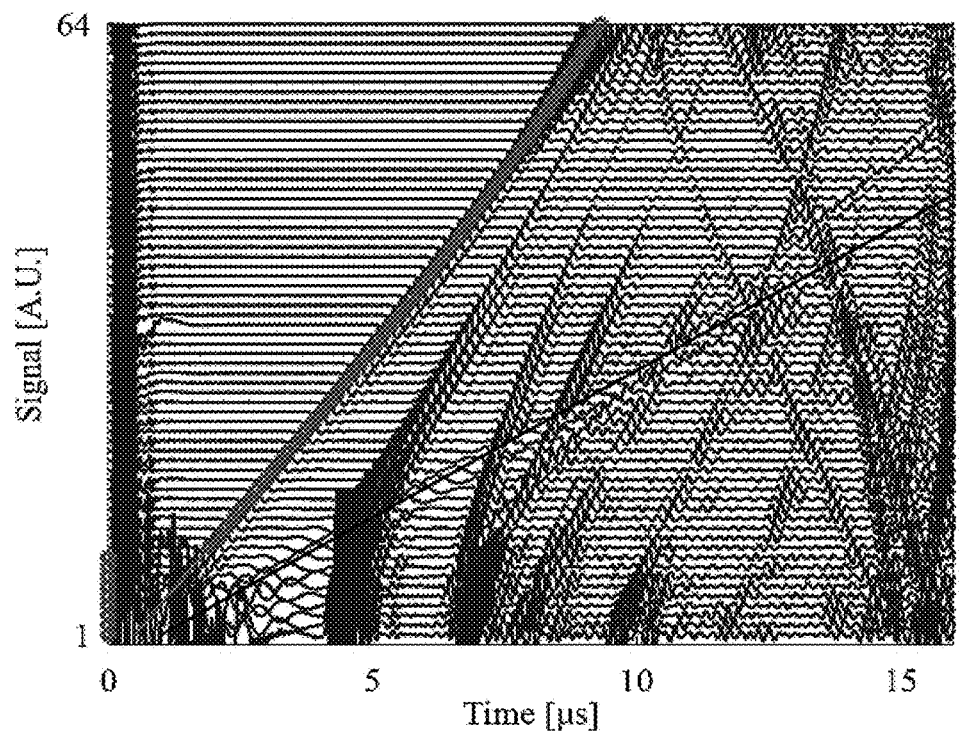
FIGS. 14A and 14B are cascade plots calculated from raw scan data obtained for the first and the $32^{nd}$ transmitters of an array of element scanning the sample of FIG. 10B.
Figure 14B:
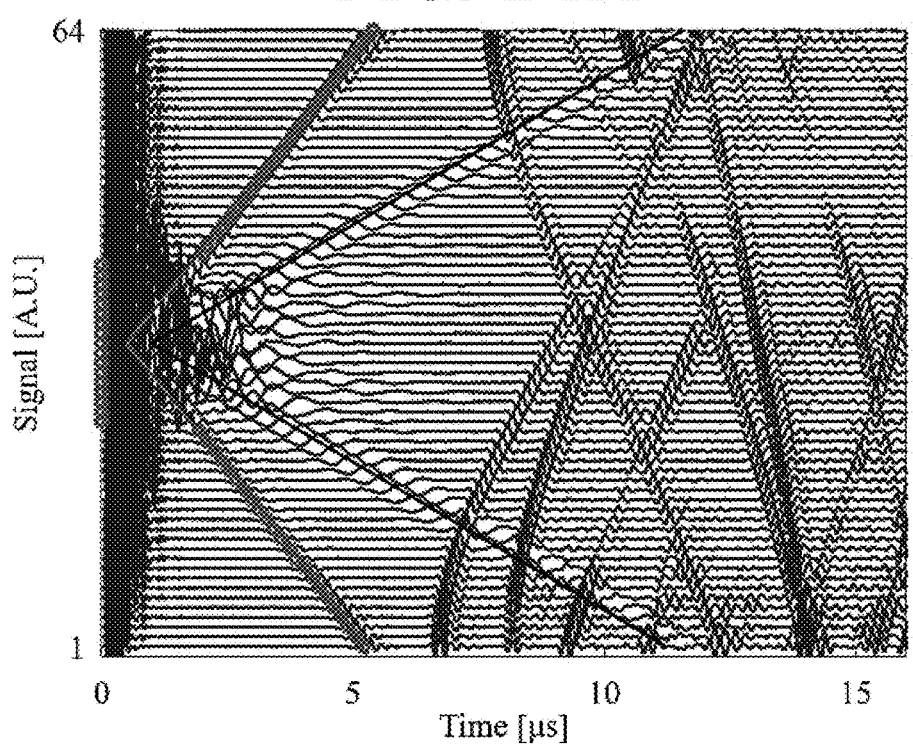

A similar analysis was performed on the complex sample (FIG. 10B). The main difference between the complex sample (FIG. 10B) and the simple sample (FIG. 10A), in terms of the array element location algorithm, is the distance between the surface the array is situated along and the nearest scatterers. In the simple sample case of FIG. 10A, the scatters were very far from the array surface, and thus the pulses arriving along the direct bulk wave paths and those of the surface waves were easy to discern. By contrast, the complex sample (FIG. 10B), the cascade plots show (FIGS. 14A and 14B, respectively for transmitting elements 1 and 32) that there are arriving scattered pulses that interfere with the surface wave pulses (the ones arriving along the black line corresponding the predicted traveltime of the Rayleigh waves). The interference indicates that the surface waves will be difficult to use in practice depending on the Rayleigh wave speed, due to the difficulty in picking their traveltimes. The bulk longitudinal wave arrival may be used because it arrives before all other waves. Thus, the bulk wave array location element code (as given in Eqs. (7-10)) is used in this example, as it was used in the simple sample case.

Figure 15A:
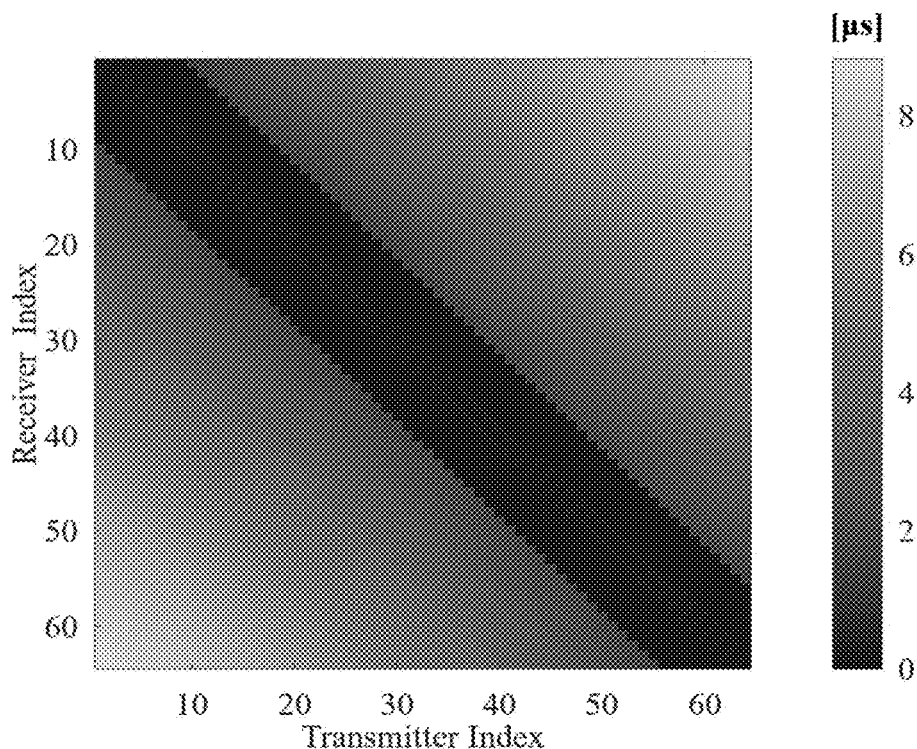
FIGS. 15A and 15B graphically illustrate measured and true traveltime matrices, respectively, from the sample of FIG. 10B.
Figure 15B:
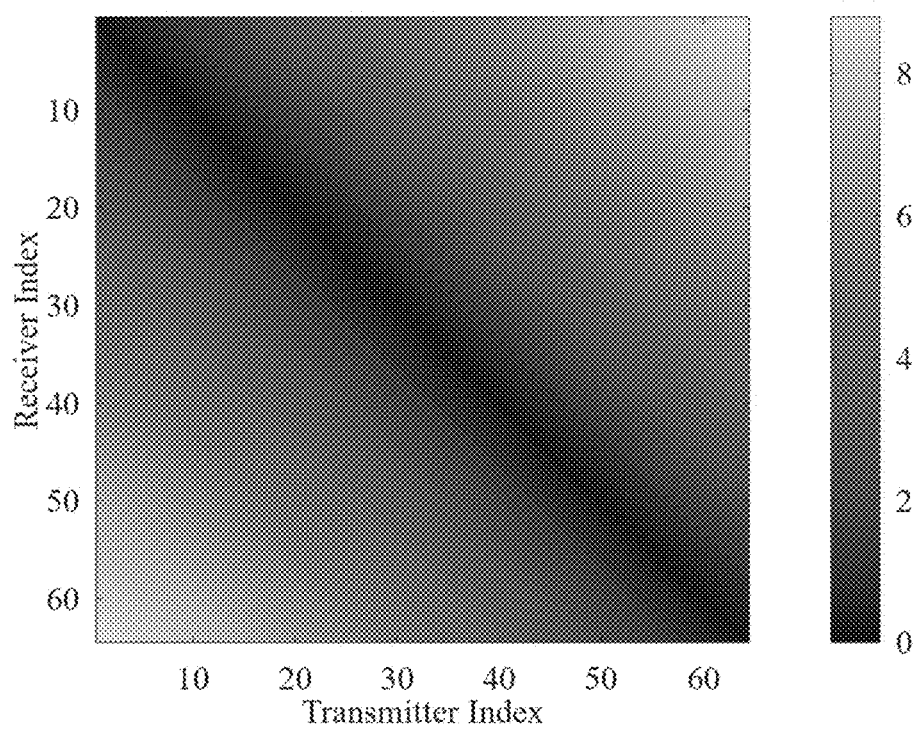

FIGS. 15A and 15B show the measured and true traveltime matrices of the complex sample, respectively. These traveltime matrices of FIGS. 15A and 15B are not significantly different from those of the simple sample (FIG. 10A), which are shown in FIGS. 12A and 12B). Similarities in these matrices may be due to direct longitudinal bulk waves traveling the same path in both samples. Thus, the bulk waves contain similar information and the same array shape may be reconstructed when the stipulations are met (i.e., the material very near the array can be considered homogenous, no scatterers exist in the region of the sample enclosed by the array, and some sets of wave paths with a clear line of sight exist between a sufficient number of array elements).

Figure 16C:
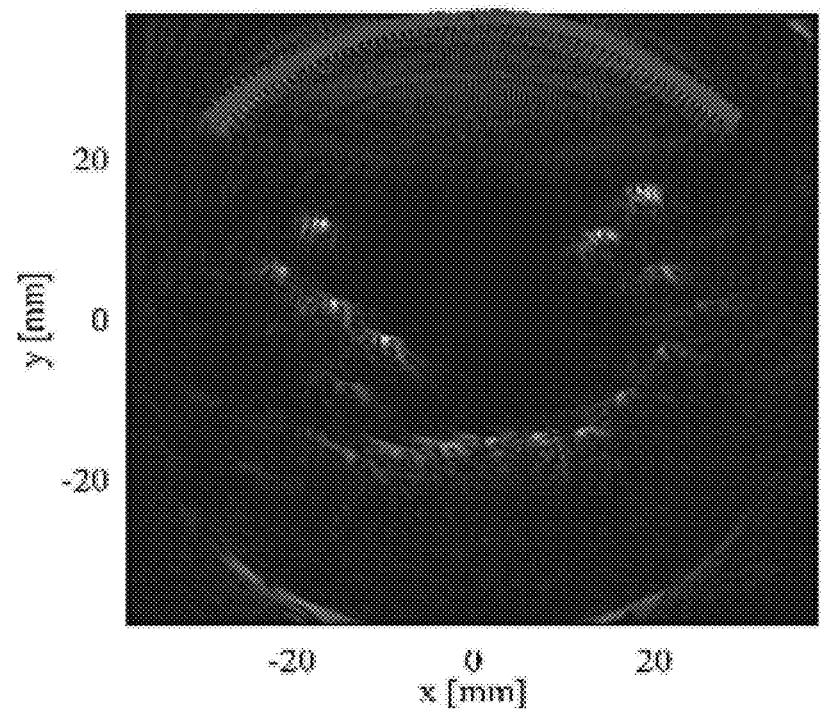
Figure 16A:
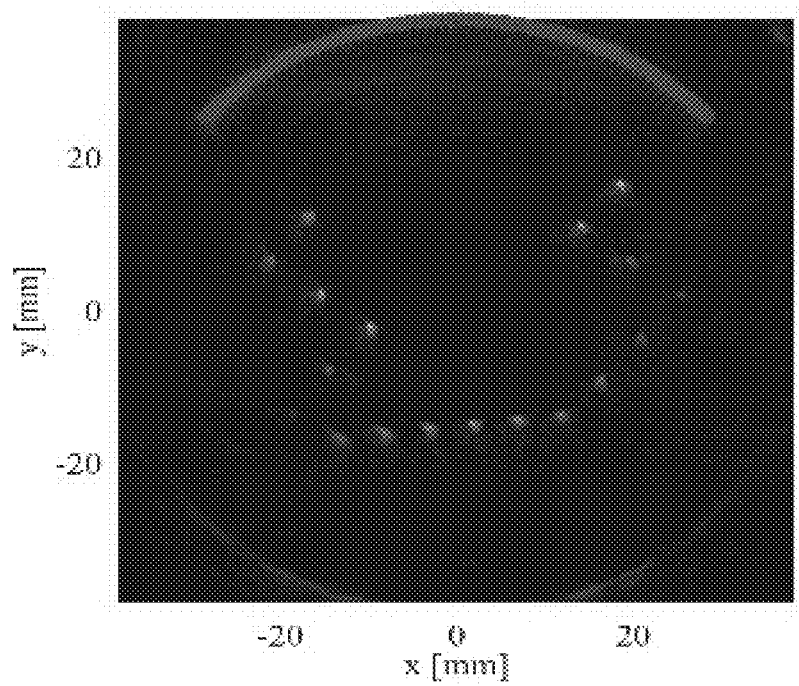
Figure 16B:
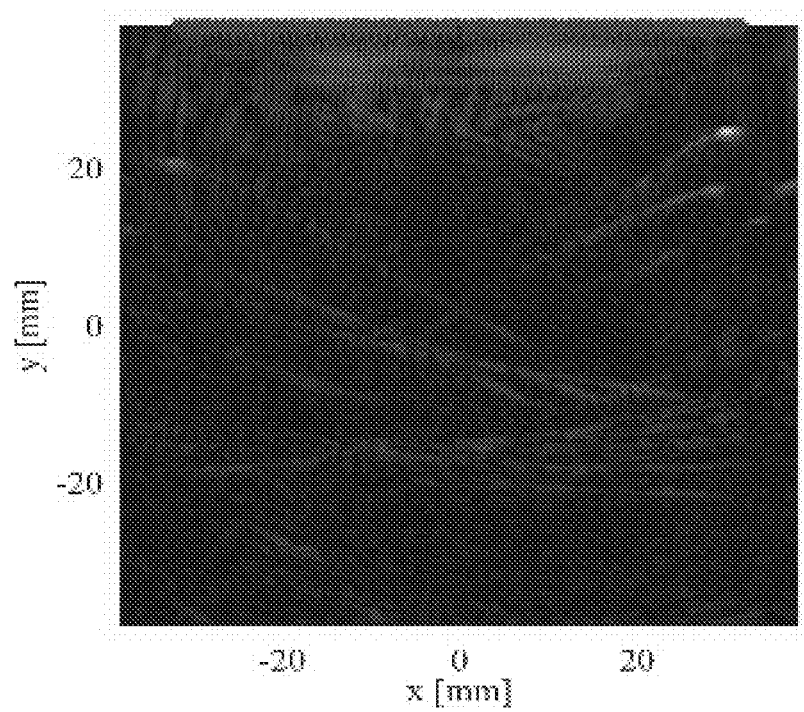

FIGS. 16A-16C are images produced by TFM using array element locations computed using the true traveltime matrix (FIG. 15B), an assumed flat linear array shape, and the array element locations computed using the measured traveltime matrix (FIG. 15A). FIG. 16A, using the true traveltime matrix of FIG. 15B as a basis to find its array element locations has good resolution with few artifacts. FIG. 16B presumes a flat array shape and exhibits extreme distortions of the resulting image. FIG. 16C is the image resulting from the use of the measured traveltimes (FIG. 15A) to find the array element locations and exhibits bright spots in the proper locations with some modest artifacts caused by slight errors in the reconstruction of the array element locations. Table 2, below, contains the mean and standard deviation of the difference between the true and estimated array element locations for the complex sample (FIG. 10B).

TABLE 2

|  | Mean [m] | Std. Dev. [m] |
| --- | --- | --- |
| x-coordinates | 4.7018e−05 | 5.7007e−05 |
| y-coordinates | −4.51845e−04 | 2.2318e−04 |

Example 2—Simulation Based Investigation of Bulk Wave Only Algorithm

Figure 17:
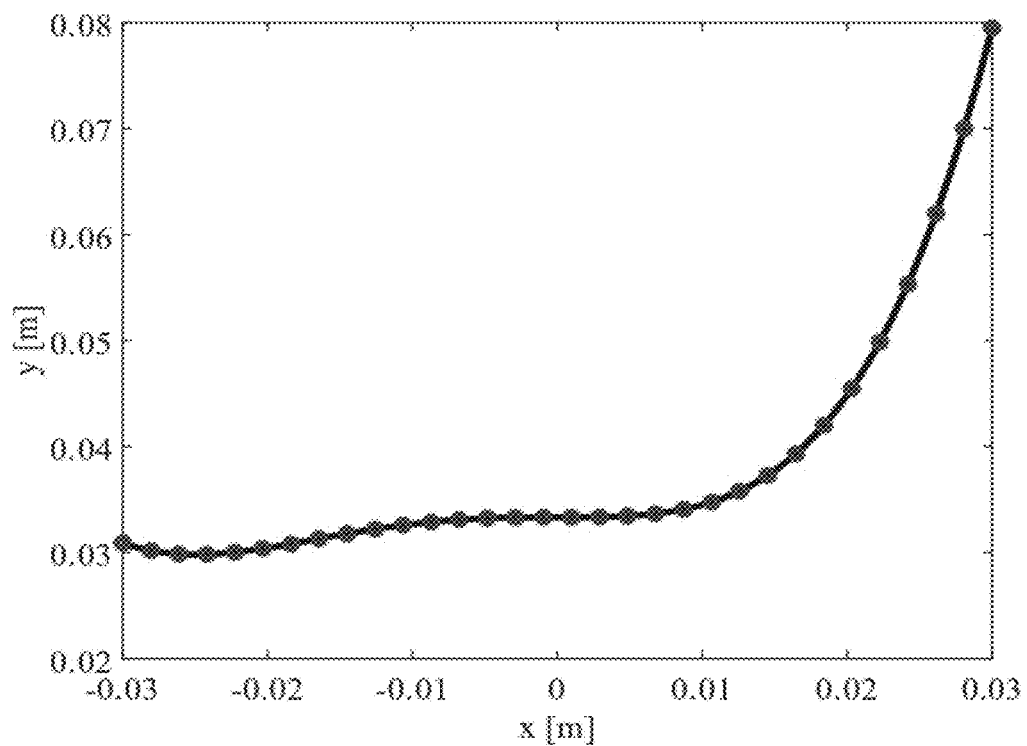
FIG. 17 is a graphical representation of a 32-element transducer array along a non-flat surface.
Figure 18:
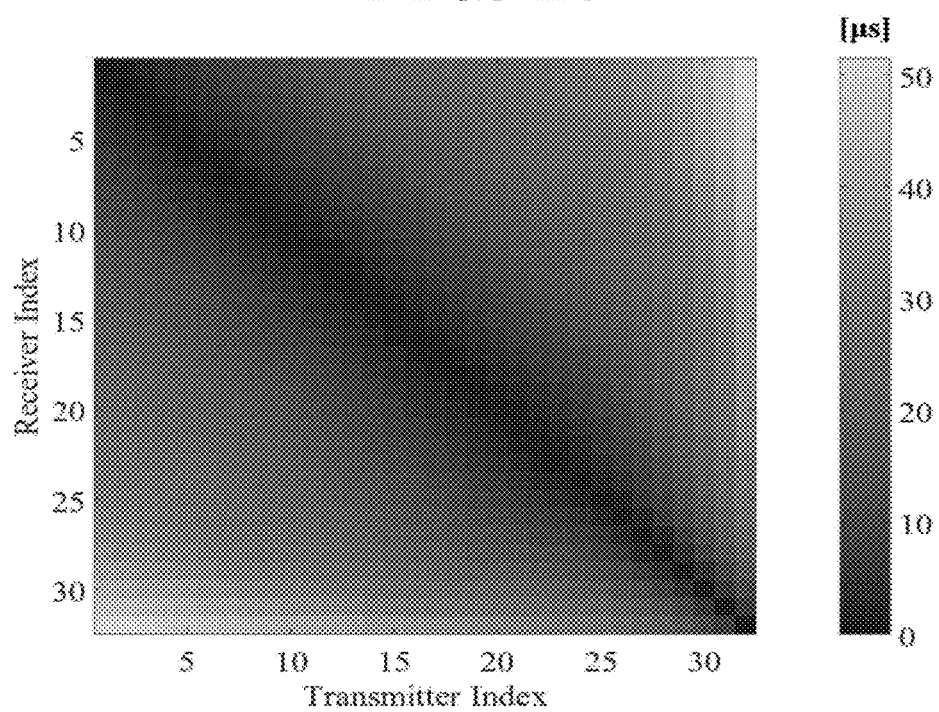
FIG. 18 graphically illustrates a measured traveltime matrix for the array shown in FIG. 17.

Referring now to FIG. 17, an exemplary problem may be used to demonstrate the optimization method according to an embodiment of the present invention by determining spatial locations of the elements of a 32-element transducer array on a non-flat surface. An arbitrary polynomial was prescribed as a boundary between the array and the medium under investigation (blue line). Thirty-two points along the polynomial were chosen to act as elements of the array and are illustrated as red dots. The background medium was prescribed to be water with wave speed, c, of 1500 m/s. FIG. 18 graphically illustrates traveltimes between each transmitter and receiver pair and was generated using Eqs. (3) and (4), the array element locations and prescribed wave speed. However, it would be understood by the skilled artisan that, in an experimental setting, actual locations of the transducers in space would not be known a priori and, thus, traveltimes would be measured from the dataset of ultrasonic signals collected from each wavepath connecting pairs of transmitters and receivers. The data of FIG. 18 was then used as an input to the algorithm along with a prescribed error cutoff level and a maximum number of iterations in an attempt to recreate the array element locations (red dots) of FIG. 17. The cutoff level is set and is the value that the objective function must reach for the optimization to cease. If the cutoff level is never reached, then the code may otherwise cease at the maximum number of iterations.

Figure 19:
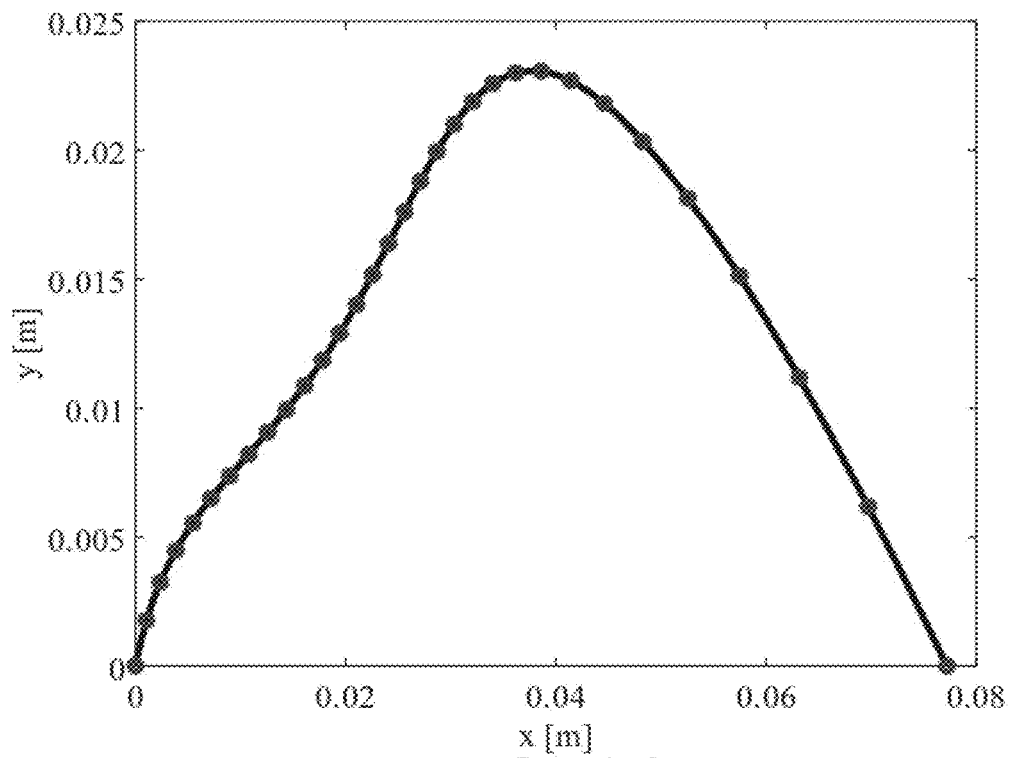
FIG. 19 graphically illustrates the reconstruction (red circles) in relation to the data from FIG. 17.

The result from the optimization algorithm is shown in FIG. 19 and matches a rotation and reflection of original curve in FIG. 17. Reconstruction element array locations (red dots) were plotted over a transformed version of the original curve (blue line) in FIG. 19. The original curve was transformed by subtracting the first array element position away from all points, and then rotated about the first array point (left most) so that the y value of the right most array element would be equal to zero, which matched the conditions set in the optimization problem. Excellent agreement was observed between the transformed original curve and the reconstructed array element locations.

Figure 20:
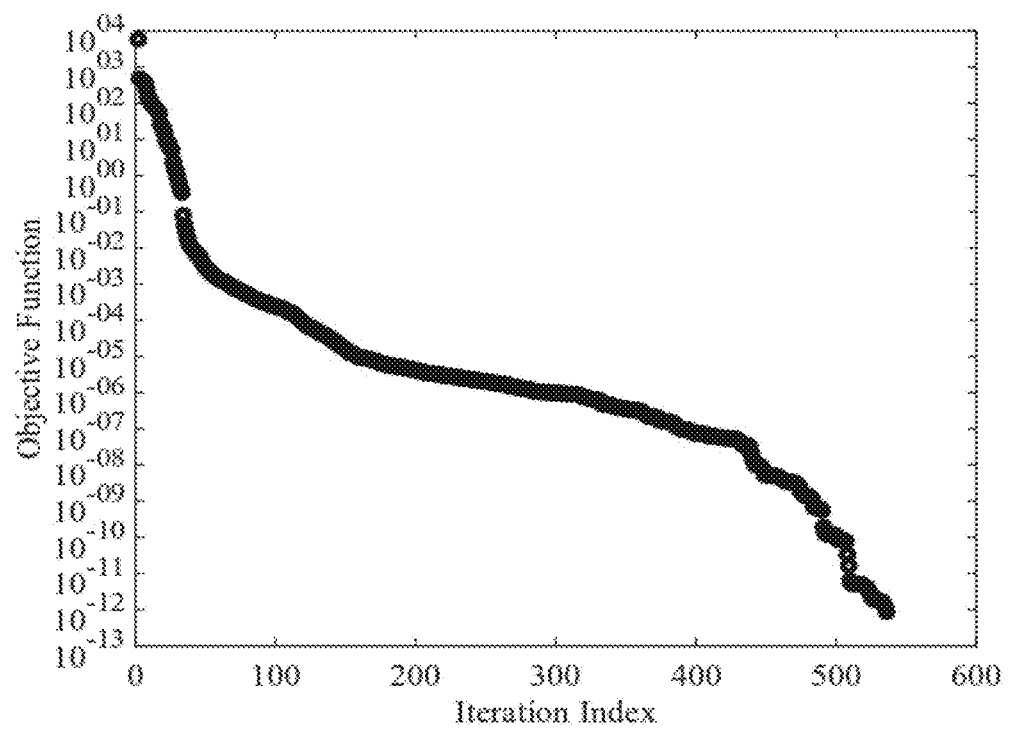
FIG. 20 graphically illustrates the objective function versus a number of iterations of the optimization algorithm.

A plot of the objective function versus a number of iterations is shown in FIG. 20.

Example 3—Simulation Based Investigation of Bulk Wave Only Algorithm Robustness to Dropped Data To demonstrate a robustness of the algorithm, some traveltime data of Example 2 was discarded and the algorithm is run again. The amount of overall data used to solve for the element positions was reduced and it would be expected to cause errors or increased solution times (i.e., number of iterations). Transmitters were selected by drawing a random number from a uniform distribution, defined from 0 to 1. If the random number was greater than 0.55, then a subsection of receivers was selected by first randomly drawing the beginning and then the ending index, which defined the bank of receivers to be discarded. The number of dropped receivers per transmitter was limited to, at most, a quarter of the total number of array elements.

Figure 21:
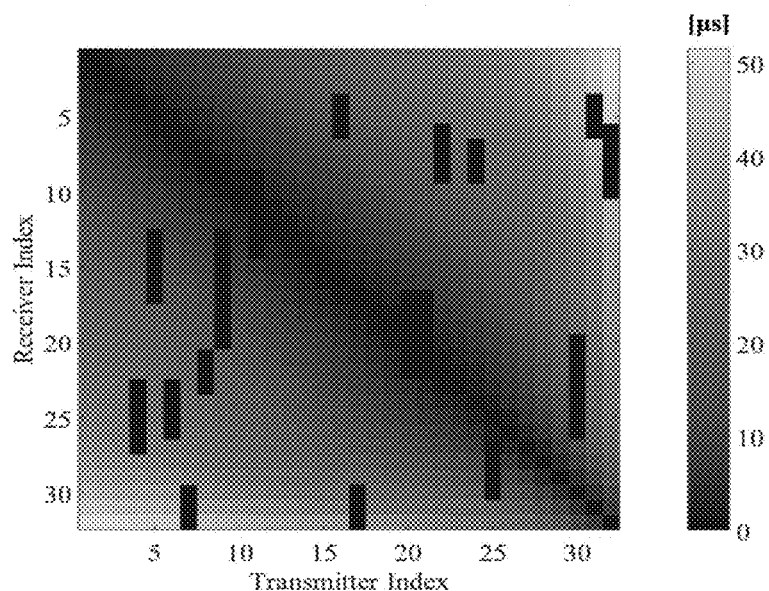
FIG. 21 graphically illustrates a measured traveltime matrix for the array shown in FIG. 17 having some of the element data removed (dark blue bars).

FIG. 21 presents the traveltime matrix with dropped data (i.e., FIG. 18 with some data removed).

Figure 22:
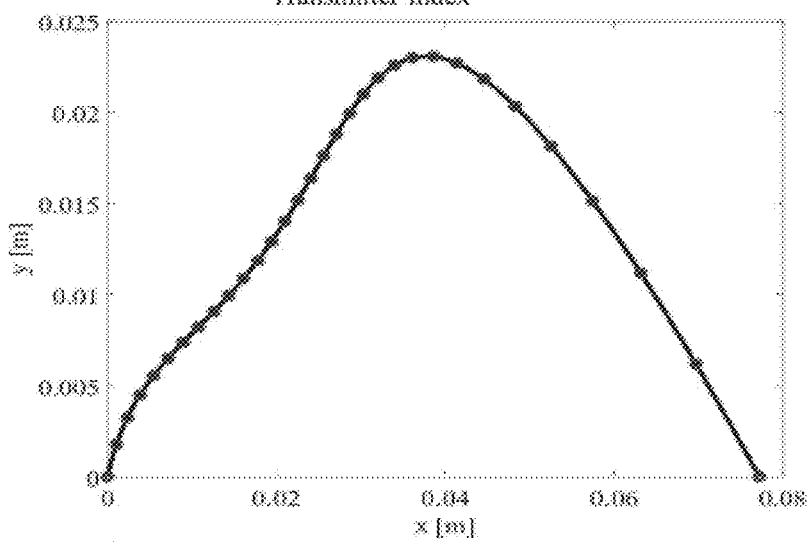
FIG. 22 graphically illustrates results from an optimization algorithm for positions of the elements of the array illustrated from FIG. 17 calculated from the traveltime matrix of FIG. 21.
Figure 23:
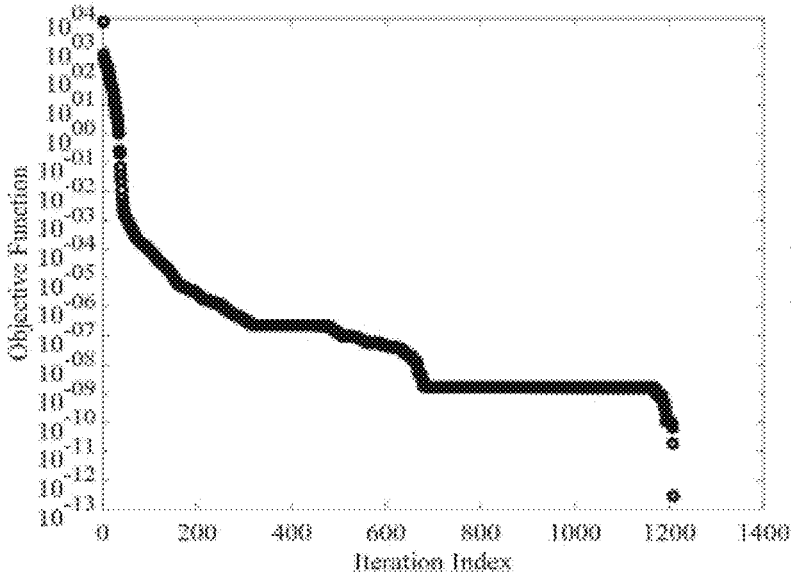
FIG. 23 graphically illustrates the objective function versus a number of iterations of the optimization algorithm.

FIG. 22 illustrates the reconstructed array element positions (red dots) and rotated and reflected original curve (blue line). FIG. 23 illustrates the objective function versus iteration curve. In spite of the reduced amount of data, good agreement was obtained in the reconstructed array shape. It was observed that about 1,200 iterations were required to meet the error criteria (compare to approximately 540 iterations required Example 2 to yield FIG. 20). As such, it may be presumed the algorithm will function best with the most possible data but may be considered robust against dropped data that might come about due to difficulty in picking traveltimes accurately.

Example 4—TFM Imaging Correction by Array Element Location Using the Bulk Wave Only Algorithm To test the impact of the array element location algorithm according to an embodiment of the present invention to imaging applications, a set of time domain signals were simulated using the technique presented in C. HOLMES (referenced above). Images were subsequently formed to compare the impact of correct array element positions versus incorrect array element positions. In this example, elements of the array were considered to be point sources and associated directivity function equal to unity.

Figure 24:
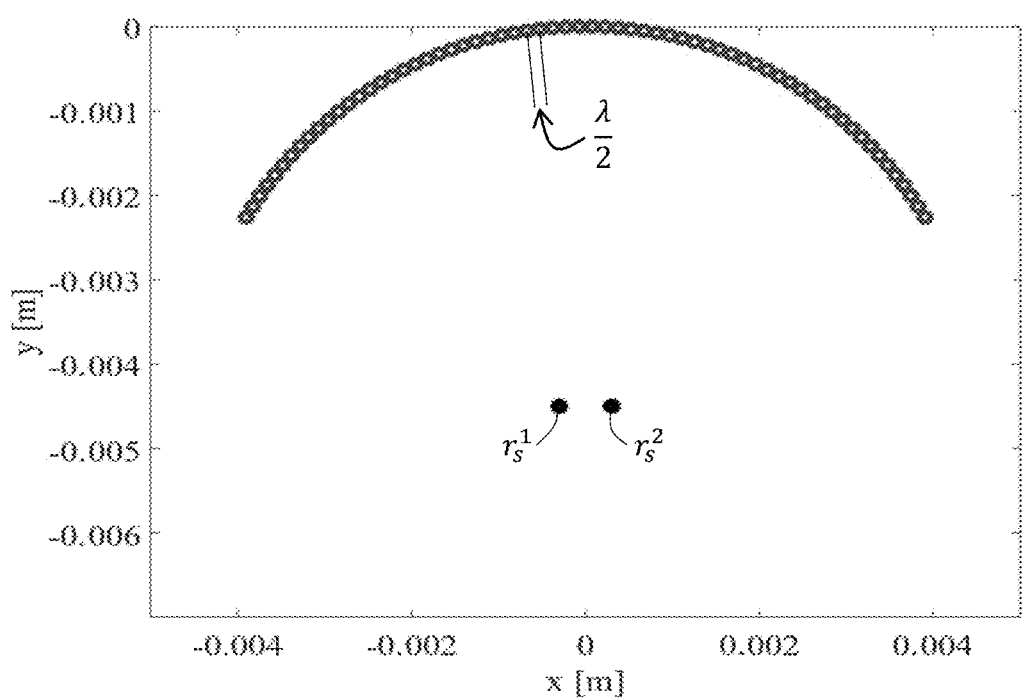
FIG. 24 schematically illustrates a model having two scatter points positioned at a distance from a semicircular array of elements.

As shown in FIG. 24, two scatter points were positioned at $r_s = \{\pm\lambda, -15\lambda\}^t$ (where $\lambda = c/f_c$ and $f_c$ is the wave packet center frequency) and wherein the superscript t indicates a transpose operation. Elements of a semicircular array were spaced (centers of adjacent elements) at a distance equal to $\lambda/2$, which is consistent with the Nyquist criteria ensuring that image artifacts (errors) do not develop due to poor wavefield sampling. The array had 64 elements, a radius of curvature of $15\lambda$, and a center frequency of 5 MHz.

Figure 25A:
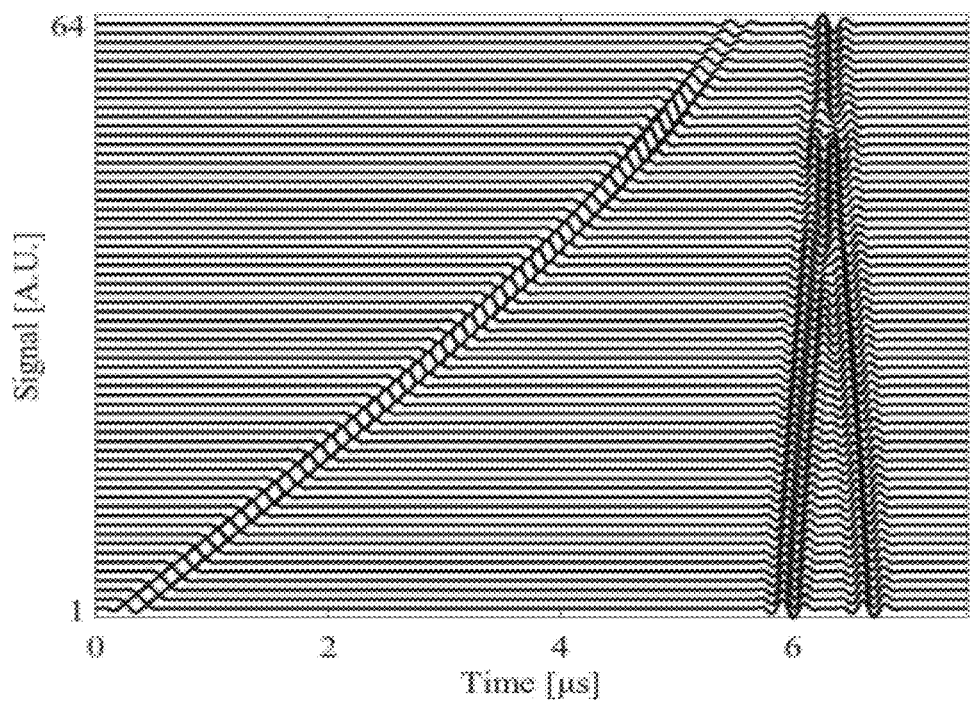
FIGS. 25A and 25B are cascade plots calculated from raw scan data obtained for the first and the $32^{nd}$ transmitters of an array of element scanning the sample of FIG. 24.
Figure 25B:
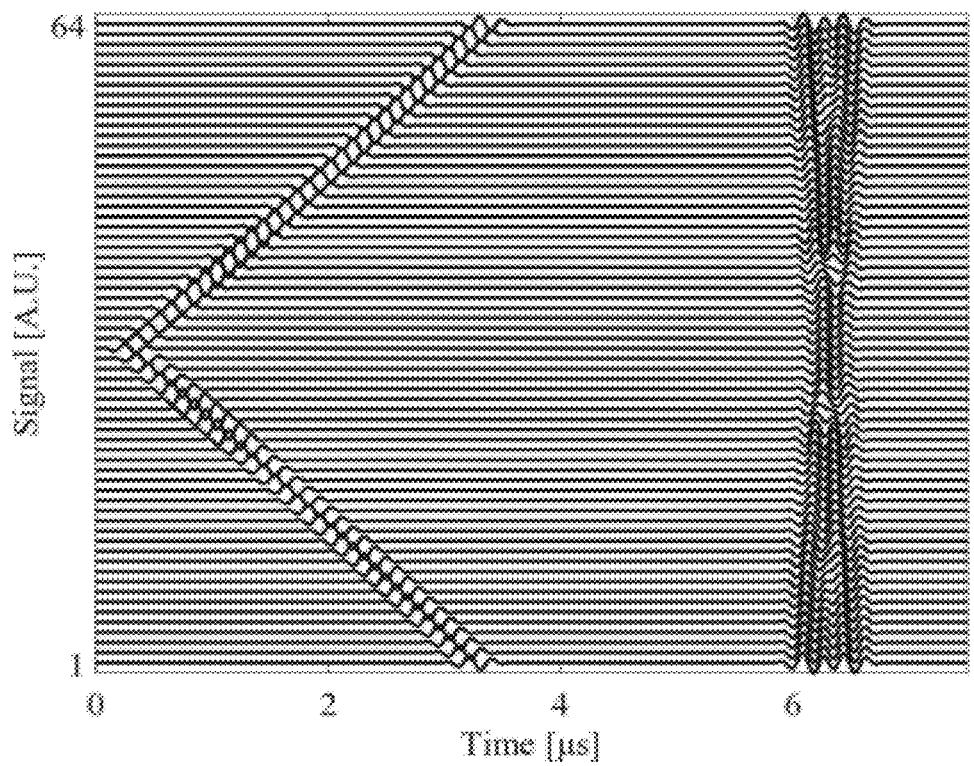

FIGS. 25A and 25B are cascade plots (i.e., a set of peak amplitude normalized signals plotted such that the mean value of each is shifted to its receiver index) of received signals when the first (FIG. 25A) and $32^{nd}$ (FIG. 25B) elements of the array were transmitting. Two main sections of wave packets are demonstrated: (1) the direct bulk waves of the incident wave, and (2) the wave packets of the scattered field (around 6 µs).

Figure 26A:
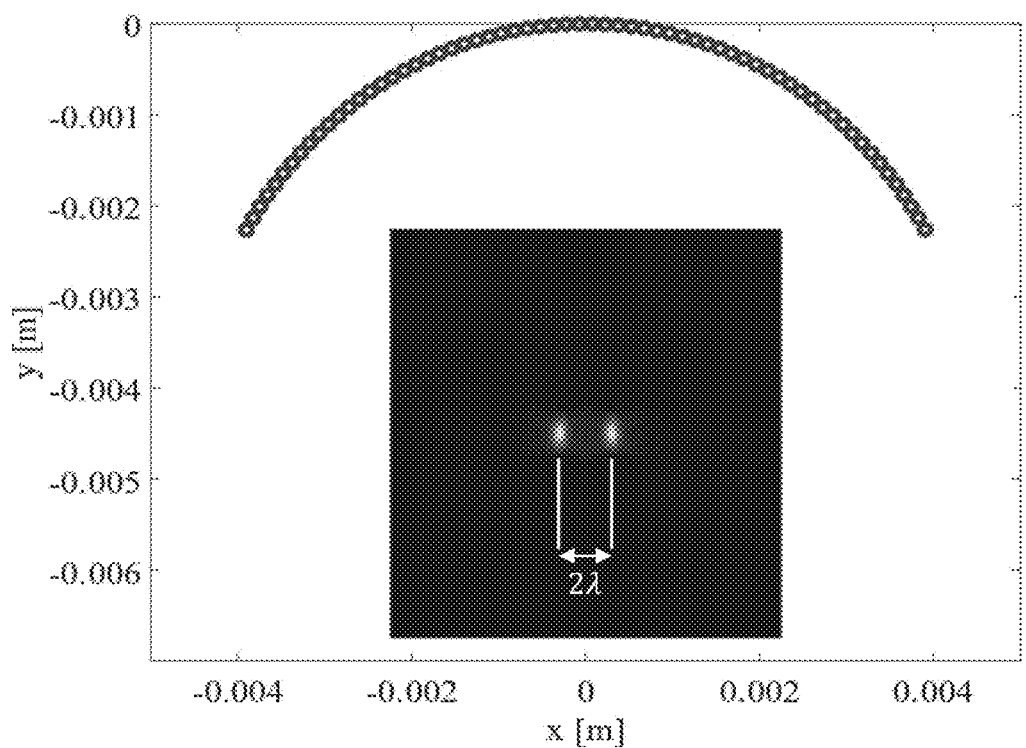
Figure 26B:
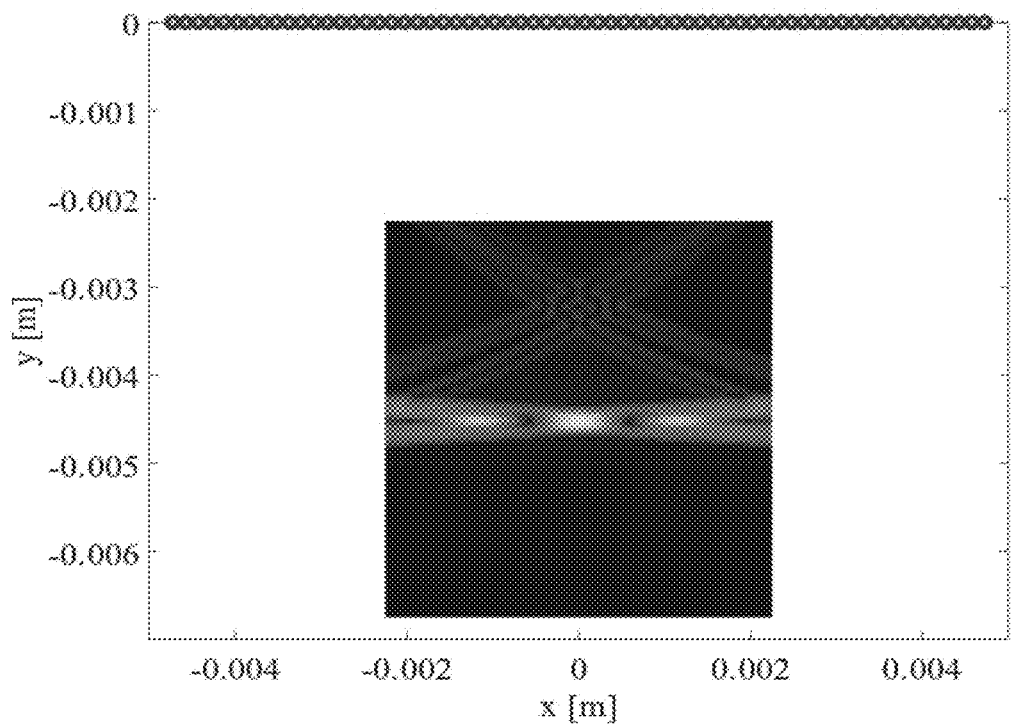
Figure 26C:
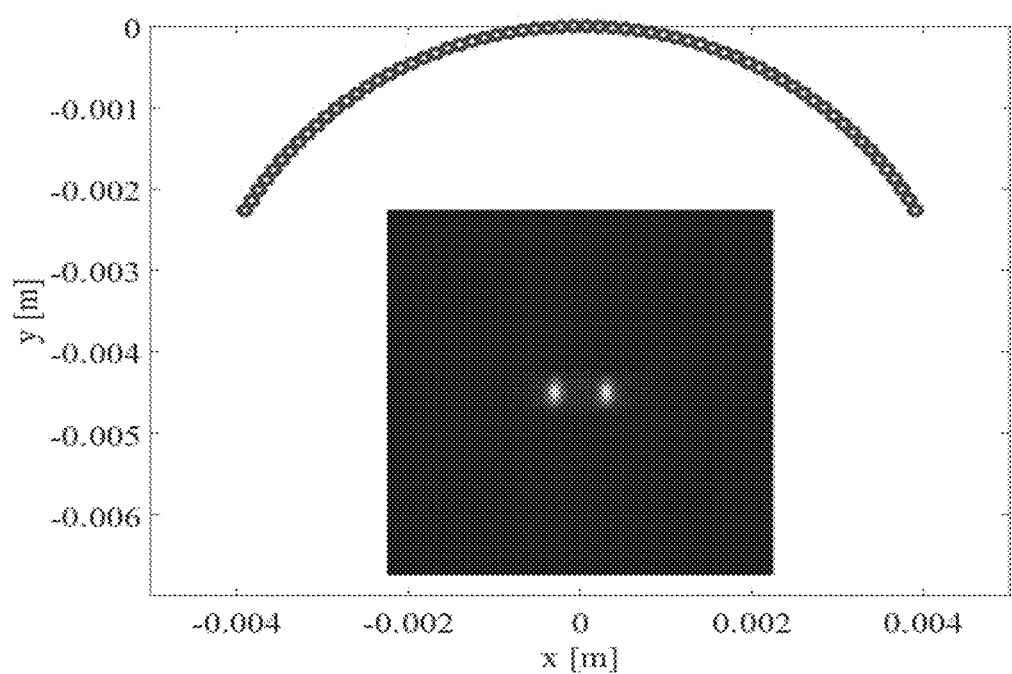

A TFM image made using the true array locations of FIG. 24 is provided in FIG. 26A. Element locations with correct spacing but infinite radius of curvature (i.e., flat) are shown in FIG. 26B. FIG. 26C illustrates element locations estimated by the element locating algorithm, as well as the image produced by TFM when using the reconstructed array element locations.

Excellent agreement was observed between the point scatterer locations shown in FIG. 24 and the reconstructed point scatterer centers (bright spots) in FIGS. 26A and 26C. Furthermore, good agreement was obtained between the true array element positions (red circles) of FIGS. 24 and 26A with those of the estimated array element positions shown in FIG. 26C. There was a degradation in the quality of the image shown in FIG. 26B, resulting from incorrect array curvature as the TFM algorithm is unable to properly focus when the array elements positions supplied to the TFM algorithm are incorrect.

A comparison of an absolute value of difference between the true and estimated array element coordinates is presented in Table 3 (wavelength was $1.5 \times 10^{-4}$ m), below. The mean error and standard deviation of errors are two or three orders of magnitude below the half wavelength (i.e., the true element spacing of the array). Thus good imaging performance using the estimated array element positions was expected.

TABLE 3

|  | Mean [m] | Std. Dev. [m] |
|---|---|---|
| x-coordinates | 3.0741e−7 | 2.3876e−7 |
| y-coordinates | 2.22317e−6 | 1.9615e−6 |

As presented herein, embodiments of the present invention are directed to an algorithm that uses the information collected from waves traveling between transmitters and receivers to make the image itself. Particular to one embodiment, an example of a high quality intensity-based imaging algorithm may serve as a testbed to verify the algorithm performance. The array element location algorithm using bulk wave data is described according to at least two embodiments that include bulk waves and interface waves. Yet, the embodiments described herein but do not necessarily comprise the totality of algorithmic possibilities that could lead to a similar result.

The method according to embodiments of the present invention reproduces a reasonable approximation of the array shape and element locations that may be used to reconstruct a usable image. It should be noted, that no a priori knowledge of the surface or internal defects is assumed when performing traveltime picking or in the shape of the array, but these things could be added as constraints to the optimization algorithm to enhance the accuracy of the resulting reconstructions of the array element profile and the subsequent image.

The array elements should transmit with sufficient amplitude so that direct arrival bulk waves may be detected between all transmitter-receiver pairs. Also, the array must partially enclose a portion of the medium. In this context, partial enclosure means that the array falls on a boundary of the medium being imaged, and that that boundary is curved such that at least a few bulk wave paths exist between array elements, are well spaced, and are distributed across the array. For example, a parabolic array shape with the wave propagation medium under the curve would give only information about the array element separations (from interface waves) but not the shape of the array because the array did not enclose any of the medium (that is, no bulk wave paths between nonconsecutive array elements exist). However, if a sinusoidal variation in such a parabolic shape is added, the local bulk wave information (i.e., within each swing of the sine curve) may be sufficient to reconstruct the local shape— the bulk waves traveling between the local minima of the array shape may be enough to reconstruct the parabolic portion of the shape. As such, the algorithm operates with the proviso that the array transmission must have at least partial communication between short-range and long-range elements through the bulk, in order for the algorithm to function properly.

In this work a method for determining the unknown locations of transducer array elements from a dataset measured by the array itself is presented according to various embodiments. The datasets comprise traveltimes measured by bulk and interface wave paths between all combinations of transmitters and receivers. At least two specific embodiments are described: (1) bulk wave only and (2) bulk and interface waves.

An exemplary demonstration of the image improvement in the TFM technique is provided by comparing images resulting from correct knowledge of the array element locations, assumed array element locations consistent with a flat array shape, and finally estimated array element locations obtained by the bulk wave only algorithm. Excellent agreement was obtained between the results of the true image and the one obtained using the estimated array element locations. Conversely, when assuming that the array was flat, significant degradation in image quality in the form of artifacts (i.e., improperly formed false image features) is plainly apparent. Although all examples and derivations provided herein are for one-dimensional arrays having two-dimensional array element coordinates, there is nothing to restrict extending this method to a two-dimensional array with three-dimensional element coordinates, as well as the multiple mappings to cylindrical, spherical, and other coordinate systems.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method for locating a plurality of elements comprising a flexible ultrasound phased array, the method comprising:
    constructing a matrix of traveltimes by transmitting a signal from each one element of the plurality and receiving the signal at each of the other elements of the plurality;
    deriving traveltimes from each received signals and arraying the traveltimes into the matrix;
    establishing relative positions of the first element of the plurality to the last element of the plurality; and
    iteratively modeling locations of each element of the plurality relative to the first and last elements of the plurality to fit the matrix of traveltimes by minimizing an object function based on bulk wave signals, the object function being:

$$o = \frac{1}{2} \sum_{R=1}^{N_R} \sum_{T=1}^{N_T} e_{RT}^2,$$

where R is a receiver array element index, T is a transmitter index, and e is a difference between the squared length of the path and a distance between the positions of the transmitter and receiver.

2. The method of claim 1, wherein minimizing the object function further comprises:
   using a gradient-based optimization scheme.

3. The method of claim 1, wherein a length between a transmitting element and a receiving element is determined by:

$$l=\sqrt{(x_T-x_R)^2+(y_T-y_R)^2}.$$

4. The method of claim 1, wherein iteratively modeling locations further comprises:
   minimizing an objective function based on bulk wave signals and interface wave signals, the object function being:

$$o = \frac{1}{2}\sum_{R=1}^{N_R}\sum_{T=1}^{N_T}(e_{RT}^b)^2 + \frac{1}{2}\sum_{R=1}^{N_R}\sum_{T=1}^{N_T}(e_{RT}^i)^2,$$

where R is a receiver array element index, T is a transmitter index, b is bulk wave datasets and lengths, i is interface datasets and lengths, and e is a difference between the squared length of the path and a distance between the positions of the transmitter and receiver.

5. The method of claim 4, wherein minimizing the object function further comprises:
   using a gradient-based optimization scheme.

6. The method of claim 4, wherein a length between a transmitting element and a receiving element is determined by:

$$l = \int_{s_T}^{s_R}\sqrt{\left(\frac{dx}{ds}\right)^2+\left(\frac{dy}{ds}\right)^2}\,ds,$$

where s is a coordinate defining a location along a parametric curve.

7. The method of claim 1, wherein deriving traveltimes includes using an Akaike Information Criterion, a cross-correlation algorithm, a cutoff level based algorithm, or an instantaneous frequency algorithm.

8. The method of claim 1, wherein iteratively modeling further comprises:
   deriving a measured path length from the received signals; and
   minimizing an error between the measured path lengths and the respective location iteration of the respective elements of the plurality.

9. A method of constructing an ultrasound image, the method comprising:
   locating a plurality of elements comprising a flexible ultrasound phased array by:
      constructing a matrix of traveltimes by transmitting a signal from each one element of the plurality and receiving the signal at each of the other elements of the plurality;
      deriving traveltimes from each received signals and arraying the traveltimes into the matrix;
      establishing relative positions of the first element of the plurality to the last element of the plurality; and
      iteratively modeling locations of each element of the plurality relative to the first and last elements of the plurality to fit the matrix of traveltimes by minimizing an objective function based on bulk wave signals, the object function being:

$$o = \frac{1}{2}\sum_{R=1}^{N_R}\sum_{T=1}^{N_T}e_{RT}^2,$$

where R is a receiver array element index, T is a transmitter index, and e is a difference between the squared length of the path and a distance between the positions of the transmitter and receiver; and
      utilizing the modeled locations of each element of the plurality to construct the ultrasound image.

10. The method of claim 9, wherein minimizing the object function further comprises:
    using a gradient-based optimization scheme.

11. The method of claim 9, wherein a length between a transmitting element and a receiving element is determined by:

$$l=\sqrt{(x_T-x_R)^2+(y_T-y_R)^2}.$$

12. The method of claim 9, wherein iteratively modeling locations further comprises:
    minimizing an objective function based on bulk wave signals and interface wave signals, the object function being:

$$o = \frac{1}{2}\sum_{R=1}^{N_R}\sum_{T=1}^{N_T}(e_{RT}^b)^2 + \frac{1}{2}\sum_{R=1}^{N_R}\sum_{T=1}^{N_T}(e_{RT}^i)^2,$$

where R is a receiver array element index, T is a transmitter index, b is bulk wave datasets and lengths, i is interface datasets and lengths, and e is a difference between the squared length of the path and a distance between the positions of the transmitter and receiver.

13. The method of claim 12, wherein minimizing the object function further comprises:
    using a gradient-based optimization scheme.

14. The method of claim 12, wherein a length between a transmitting element and a receiving element is determined by:

$$l = \int_{s_T}^{s_R}\sqrt{\left(\frac{dx}{ds}\right)^2+\left(\frac{dy}{ds}\right)^2}\,ds,$$

where s is a coordinate defining a location along a parametric curve.

15. The method of claim 9, wherein deriving traveltimes includes using an Akaike Information Criterion, a cross-correlation algorithm, a cutoff level based algorithm, or an instantaneous frequency algorithm.

16. The method of claim 9, wherein iteratively modeling further comprises:
    deriving a measured path length from the received signals; and
    minimizing an error between the measured path lengths and the respective location iteration of the respective elements of the plurality.

* * * * *